(12) United States Patent
Carrel et al.

(10) Patent No.: US 8,696,625 B2
(45) Date of Patent: Apr. 15, 2014

(54) INJECTION SET AND INJECTION ASSISTANCE DEVICE

(75) Inventors: Franck Carrel, Pont de Claix (FR); Frederic Perot, Saint Paul de Varces (FR); Laurent Barrelle, Saint Nizier du Moucherotte (FR); Eric Olive, Vif (FR); Jean-Pierre Grimard, Vif (FR); Samuel Gagnieux, Bresson (FR)

(73) Assignee: Becton Dickinson France, Le Pont de Claix (FR)

( * ) Notice: Subject to any disclaimer, the term of this patent is extended or adjusted under 35 U.S.C. 154(b) by 1042 days.

(21) Appl. No.: 11/912,249

(22) PCT Filed: Apr. 19, 2006

(86) PCT No.: PCT/IB2006/001419
§ 371 (c)(1),
(2), (4) Date: Jun. 9, 2008

(87) PCT Pub. No.: WO2006/111862
PCT Pub. Date: Oct. 26, 2006

(65) Prior Publication Data
US 2011/0245770 A1 Oct. 6, 2011

(30) Foreign Application Priority Data

Apr. 20, 2005 (FR) ...................................... 05 03963
Apr. 20, 2005 (FR) ...................................... 05 03964

(51) Int. Cl.
*A61M 5/46* (2006.01)

(52) U.S. Cl.
USPC ............ 604/117; 604/125; 604/184; 604/192

(58) Field of Classification Search
USPC ......... 604/117, 121, 124–125, 134–137, 181, 604/183–184, 187, 192–198; 128/919; 600/432
See application file for complete search history.

(56) References Cited

U.S. PATENT DOCUMENTS

| | | | | |
|---|---|---|---|---|
| 5,176,643 | A * | 1/1993 | Kramer et al. | ................ 604/135 |
| 5,634,906 | A * | 6/1997 | Haber et al. | ................ 604/136 |
| 6,939,330 | B1 * | 9/2005 | McConnell-Montalvo et al. | ............. 604/197 |
| 2003/0014018 | A1 | 1/2003 | Giambattista | |
| 2005/0033230 | A1 | 2/2005 | Alchas | |

FOREIGN PATENT DOCUMENTS

| WO | WO03/074111 | 9/2003 |
|---|---|---|
| WO | 2004/060445 A2 | 7/2004 |

* cited by examiner

*Primary Examiner* — Quynh-Nhu H Vu
(74) *Attorney, Agent, or Firm* — Hoffmann & Baron, LLP

(57) ABSTRACT

The present invention relates to an injection assistance device (1) comprising a body (2) with a needle (7), grasping means (4) and first elastic return means (9) to dampen limited movement of said grasping means (4), in at least one of the two directions, respectively distal or proximal, during an injection phase, and to maintain said body (2) in its insertion position and said needle (7) at a constant insertion length during the injection step, when the user increases, respectively releases, a distal pressure on the grasping means (4).
The invention also relates to an injection set (100) comprising an injection device (3) and the said assistance device (1).

7 Claims, 26 Drawing Sheets

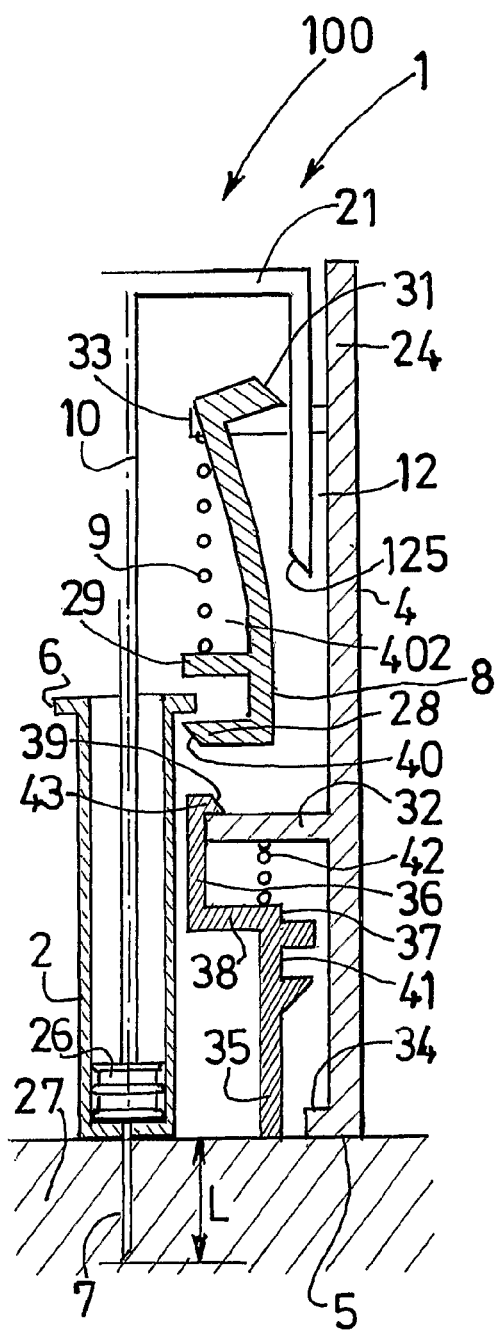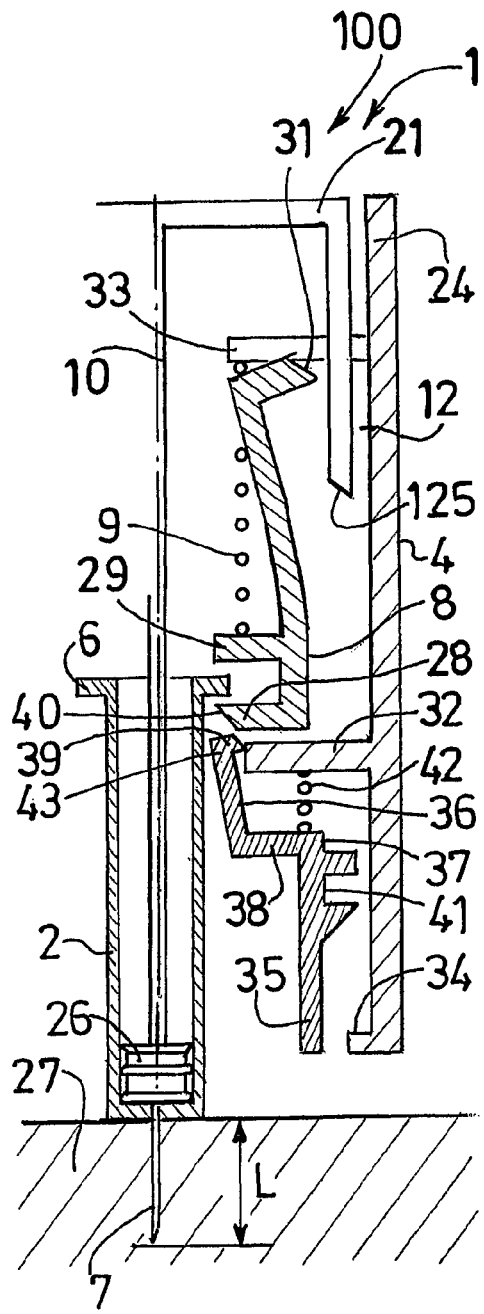

Figure 1:
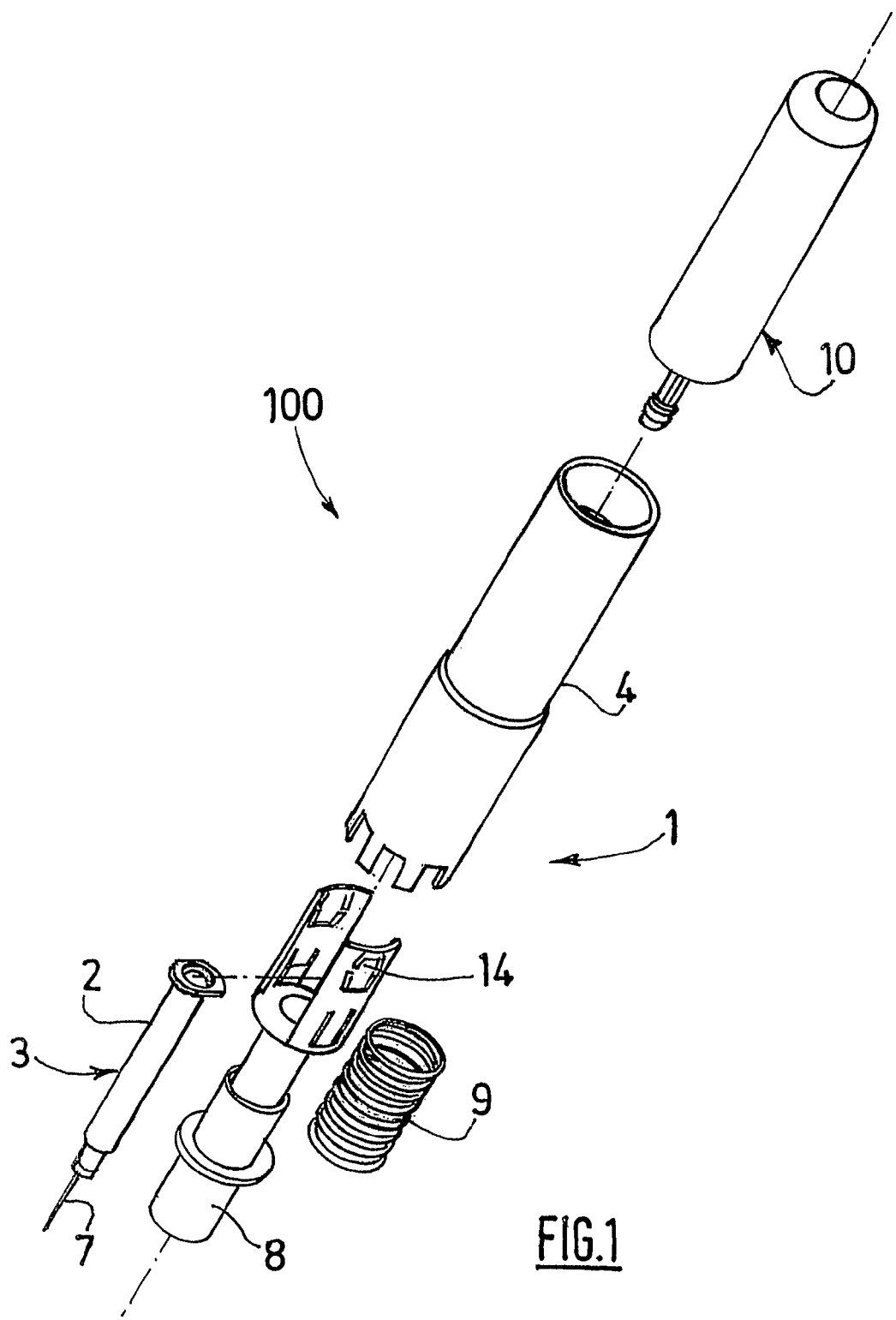

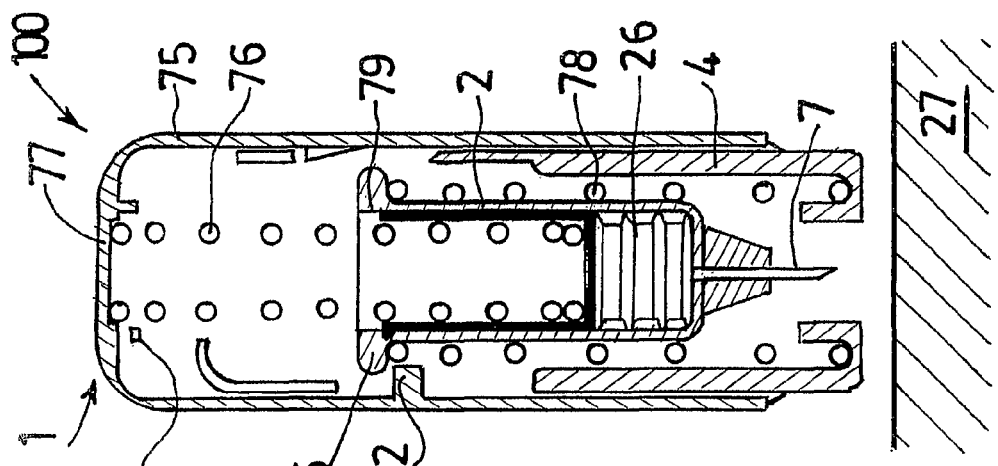
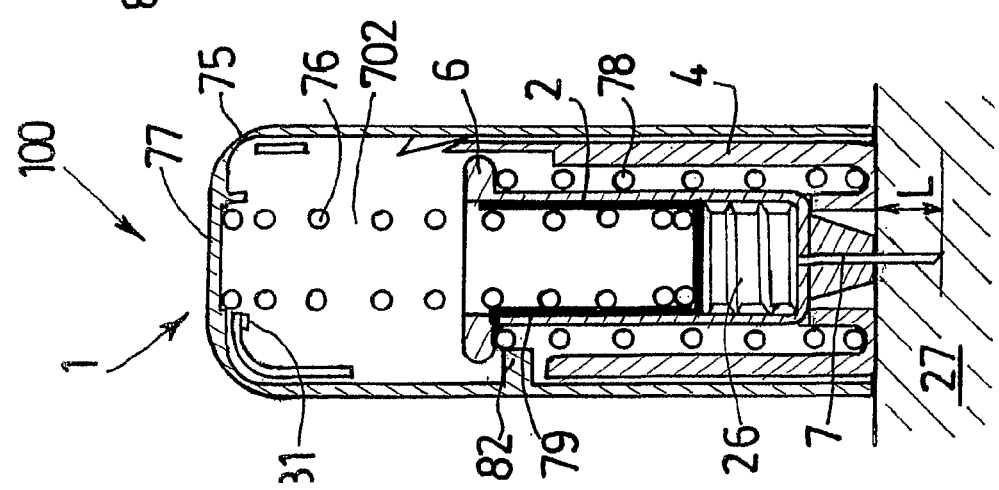
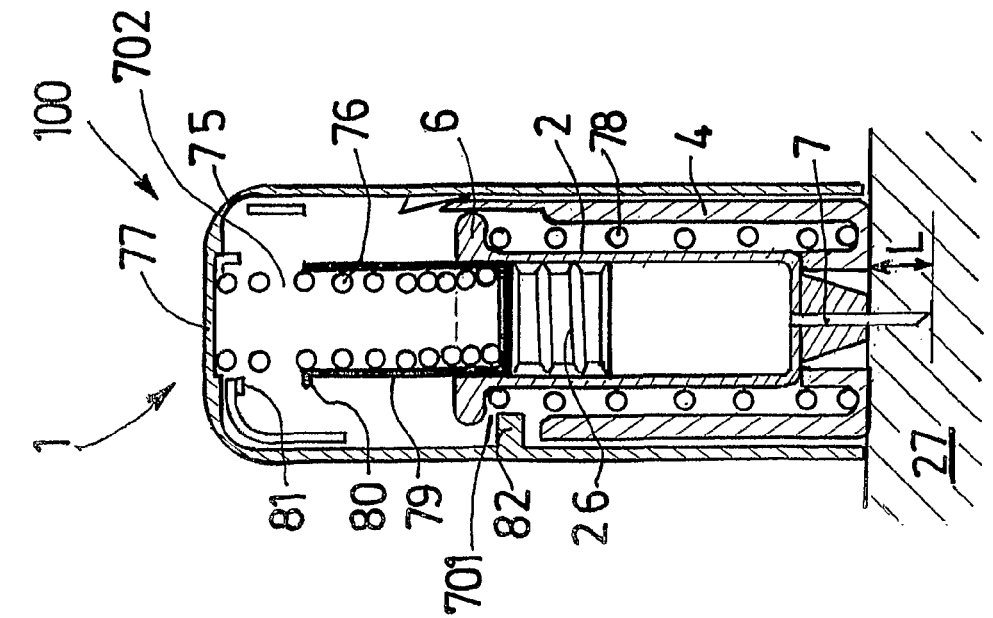

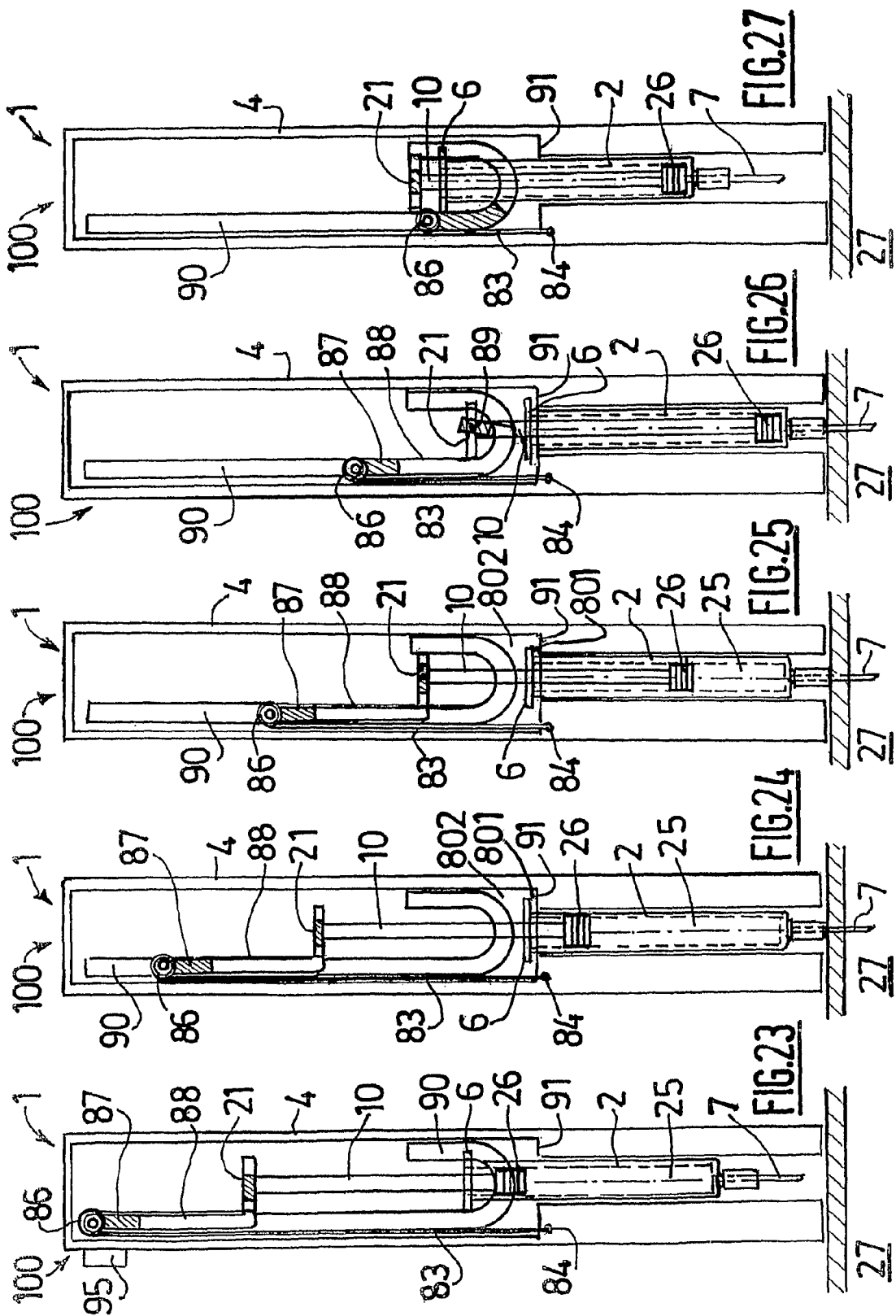

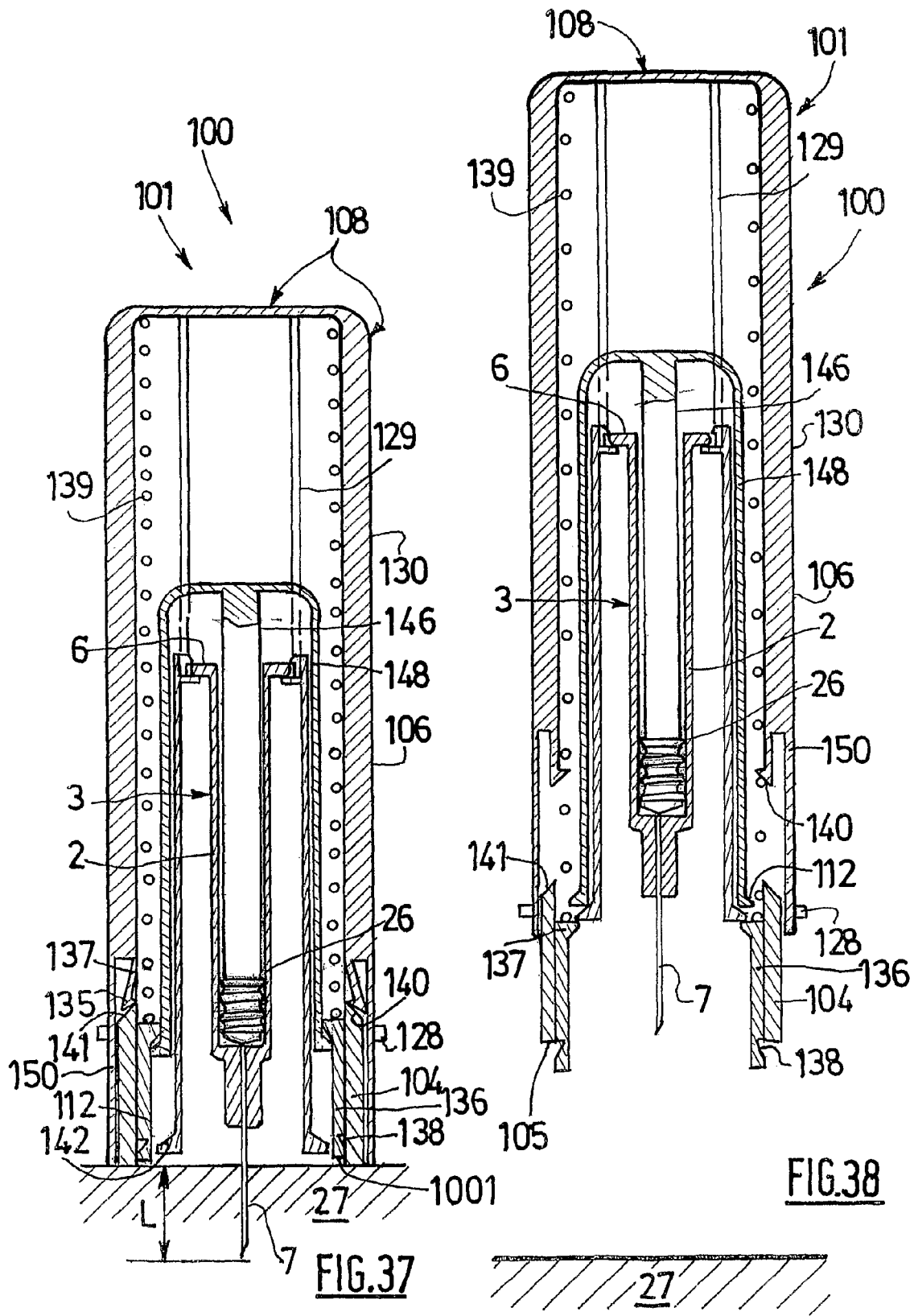

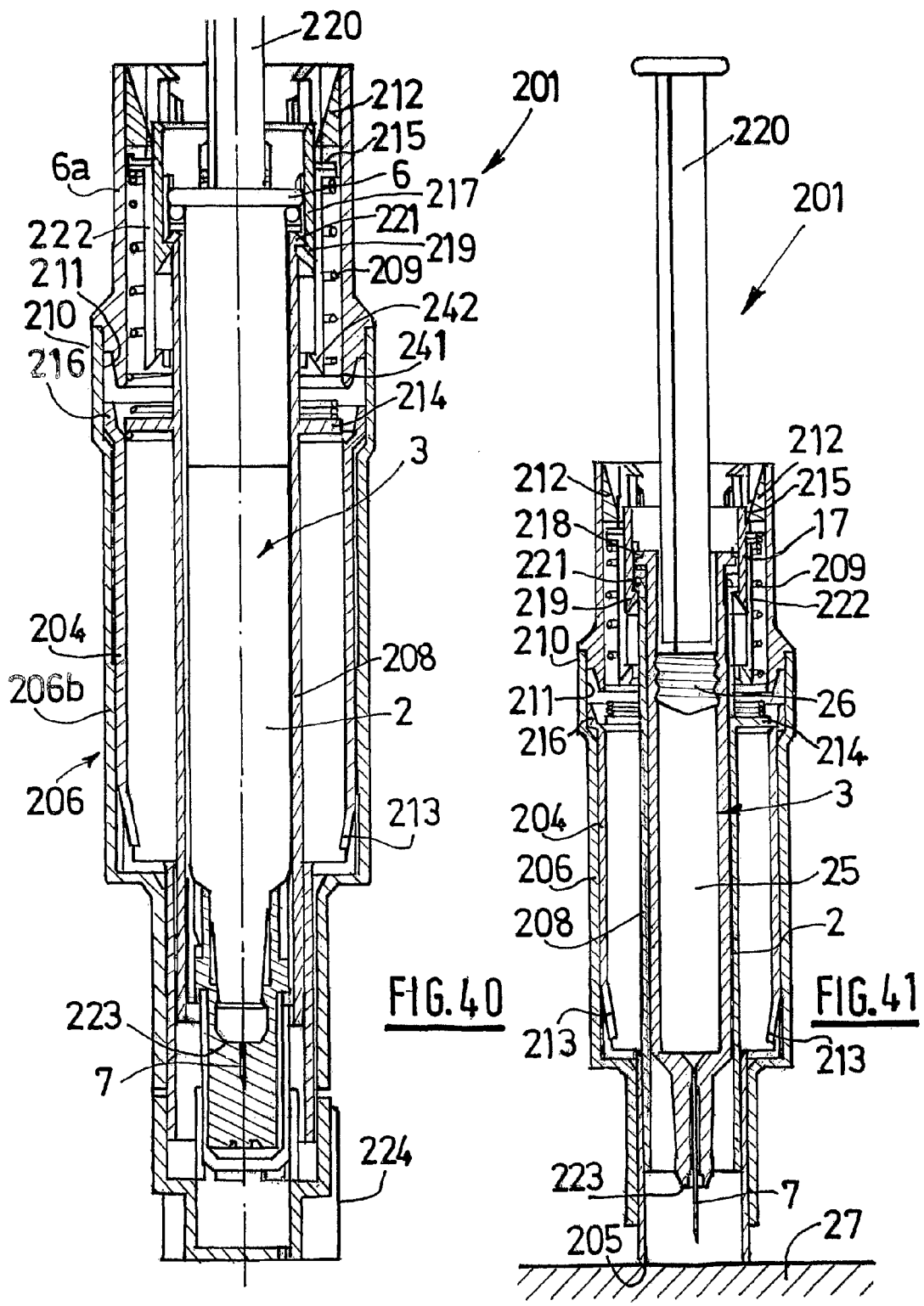

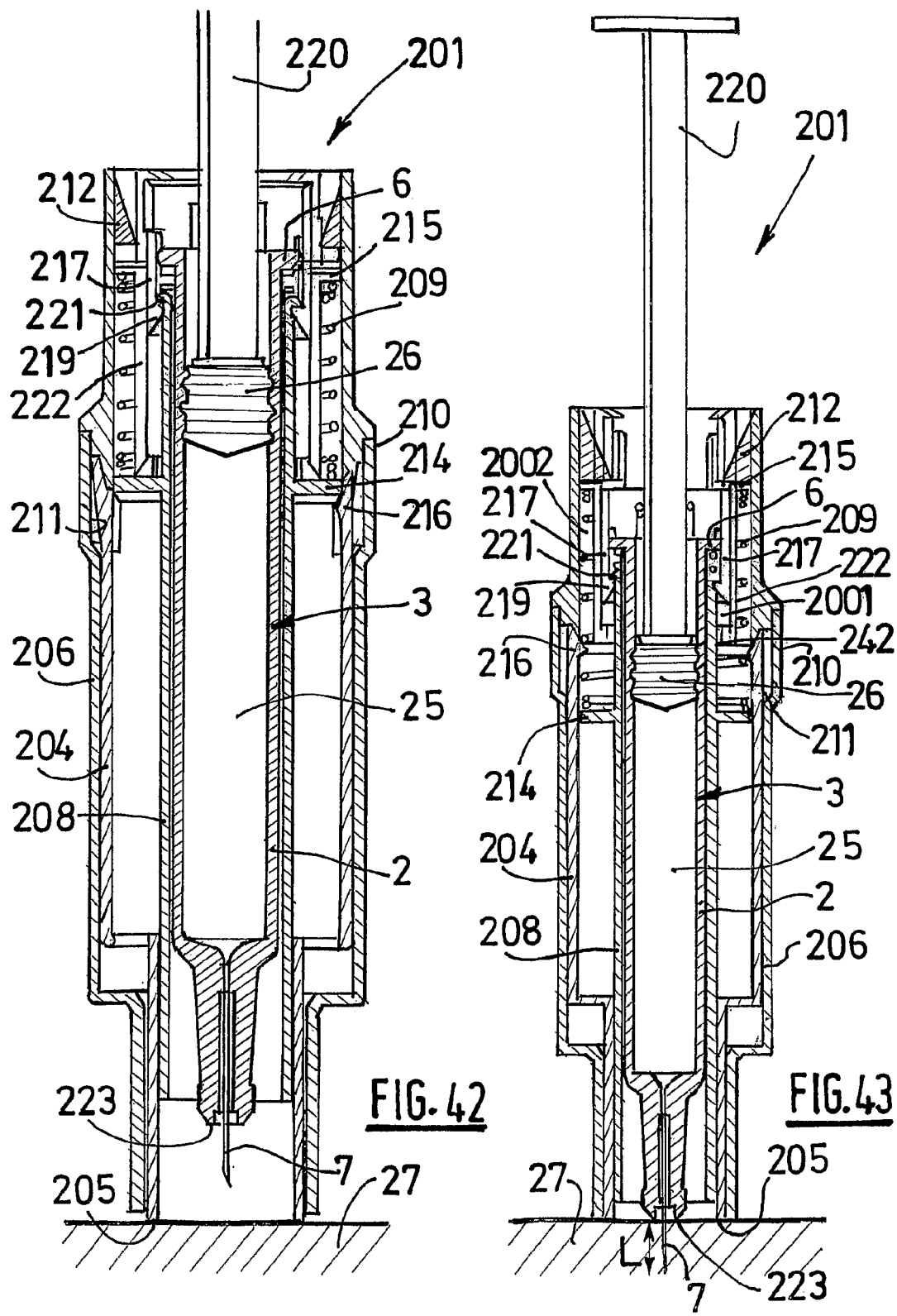

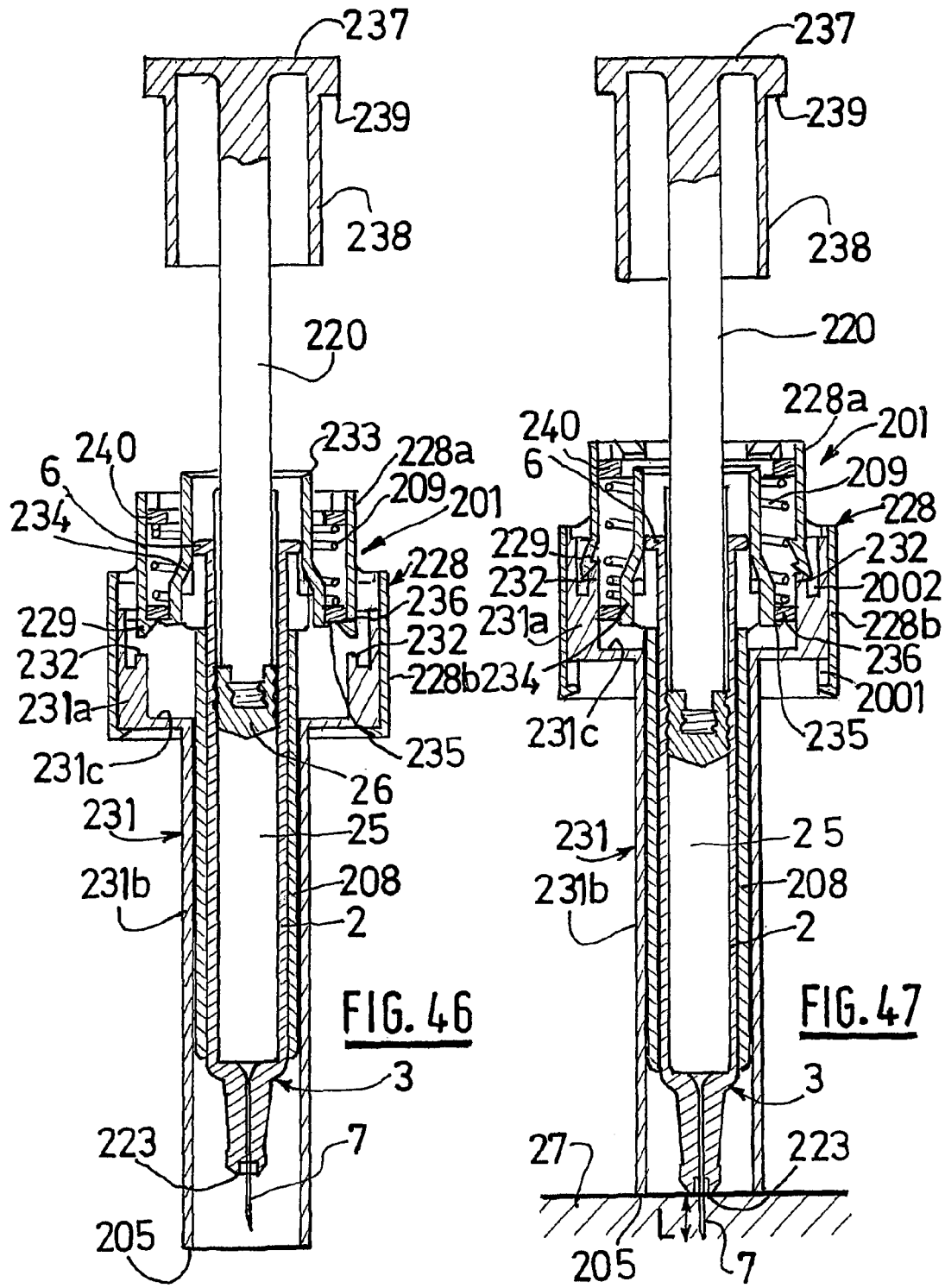

INJECTION SET AND INJECTION ASSISTANCE DEVICE

The present invention relates to an injection assistance device for an injection device and to an injection set provided with the said injection assistance device, these devices allowing a product to be injected safely and at an accurate injection depth into an injection site.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

In order to administer a medicinal product to a body, particularly the human body, there are various possible routes depending on the place in the body at which the said product is to be injected: thus, the product may be injected intravenously, intramuscularly, subcutaneously, into a joint, or else intradermally. In many of these latter cases, and, particularly when injecting subcutaneously, the depth to which the needle is inserted and therefore at which the product is injected is particularly significant. Thus, it is possible to observe an adverse immunological reaction if, for example, a product that should have been injected into the subcutaneous tissues is finally injected into the intradermal tissues.

The operation of injecting a product using a syringe is particularly delicate. The patient may make an unforeseen movement or alternatively the person administering the injection might make a wrong move. Thus, errors in the depth to which the needle is inserted are particularly difficult to avoid and discrepancies of just a few millimeters may, themselves alone, lead to errors in injection depth.

Likewise, once the needle has been inserted, it is important to guarantee that this insertion depth is maintained throughout the injecting of the product so as to guarantee the correct injection depth.

As far as subcutaneous injection is concerned, there are various injection techniques currently used. Some users prefer to pinch the skin before inserting the needles, others prefer not to, and still others angle the syringe before inserting it into the skin, it being possible for this angle to vary from one user to another. The result of all this is that the depth to which the needle is inserted and therefore at which the product is injected may itself also vary, with the unpleasant consequences mentioned above.

Furthermore, in this kind of operation, it is also important to avoid any needlestick injury due to the exposed needle, whether this be before or after injection.

In addition, to limit the apprehension felt by the patient, particularly in the case of injections administered by the patient himself, it is desirable for the injection device not to look like a conventional syringe and/or for the needle not to be visible or to be visible only a little prior to insertion.

Finally, injecting a product using traditional injection devices generally entails at least two manual steps. For example, in the case of syringes, one manual step is to hold the body of the syringe in order to insert the needle into the injection site, another step consists in pressing on the plunger rod in order to administer the injection, the progression from one step to the other generally entailing moving the fingers with respect to the syringe.

There therefore remains a need for an injection assistance device and for an injection set which are made safe, that is to say which make it possible to limit the impact of undesired movements of the patient and/or of the user in order to prevent a variation in the depth to which the needle is inserted when administering the injection so as to avoid unintentionally injecting the said product at an inadequate depth, limiting the number of manipulations to be carried out by the user, limiting the risk of needlestick injury both to the patient and to the person administering the injection, limiting the apprehension felt by the patient and making the giving of the injection easier.

There also remains a need for such an injection assistance device and an injection set that allow the user to be certain of causing the needle to penetrate the injection site to a predetermined insertion depth and, in addition, guarantee that the injection is administered at this predetermined depth.

There also remains a need for such an injection assistance device and an injection set that allow the needle to be kept at a constant insertion length, at least during the injection step, regardless of any increase or release of distal pressure exerted by the user on the injection device.

Moreover, it is important that the user be able to adjust the dose to be injected before proceeding with any injection step and/or to perform a vein test to prevent injection in the vein.

The present invention remedies these needs by proposing Injection assistance device for an injection device for injecting a product into an injection site, this injection assistance device comprising at least one hollow body intended to receive a product that is to be injected, at least one hollow injection needle intended to penetrate the injection site, and at least one piston plunger housed in the said body, the said body and the said piston plunger being able to be moved in axial translation one with respect to the other, characterized in that the said injection assistance device comprises at least:
  grasping means intended to be manually handled by the user in order to apply said injection device on said injection site during an insertion and an injection steps, said grasping means being intended to receive at least in part, the said body and being arranged in such a way as to allow the said body axial mobility between at least a first position known as the initial position in which the said needle is not exposed over its insertion length, and a second position known as the insertion position in which the said needle is exposed by a predetermined insertion length L,
  at least first elastic return means, said first elastic return means being coupled to said body and to said grasping means, said first elastic return means being in a partially expanded state so as to dampen limited movement of said grasping means, in at least one of the two directions, respectively distal or proximal, during said injection step, and to maintain said body in its insertion position and said needle at a constant insertion length, namely said predetermined insertion length L, during the injection step, when the user increases, respectively releases, a distal pressure on the grasping means.

The injection assistance device of the invention allows the needle insertion depth to be kept constant in the insertion position and during the injection of the product, regardless of any slight movement of the grasping means. Thanks to the device of the invention, all unwanted displacement of the grasping means has very limited impact, or no impact at all on the needle insertion depth. The user is therefore certain to inject the product at the right depth even if the distal pressure he exerts on the device is not constant.

The injection assistance device according to the invention allows the injection to be administered in a minimum number of actions, particularly disposing with at least one of the two manual steps described hereinabove, and preferably dispensing with these two manual steps. Thus, the operation of administering the injection is entirely safe, the step of inserting the needle in particular being done automatically, without the user having to intervene. Any risk of error is thus avoided.

In an embodiment of the invention, said first elastic return means is arranged so as to dampen any limited distal or proximal movement of said grasping means during said injection step, and to maintain said body in its insertion position and said needle at a constant insertion length, namely said predetermined insertion length L, during the injection step, regardless of any increase or release of distal pressure exerted by the user on the grasping means.

In an embodiment of the invention, the injection assistance device is arranged in such a way that, in the insertion position, said grasping means are separated from said body, or from an element coupled to said body at least in said insertion position, by a gap that allows the said grasping means to move with respect to said body or to said element, when distal pressure exerted on said grasping means is released.

In an embodiment of the invention, the injection assistance device is arranged in such a way that, in the insertion position, said grasping means are separated from said body, or from an element coupled to said body at least in said insertion position, by a space that allows the said grasping means to move with respect to said body or to said element, when distal pressure exerted on said grasping means is increased.

In an embodiment of the invention, the injection assistance device further comprises final protection means arranged in such a way as to cover the said needle in a post-injection final protection position, which final protection means are able to move in translation with respect to the said body between an injection position in which the needle is exposed and a final protection position in which the needle is covered.

In an embodiment of the invention, the injection assistance device comprises automatic-activation means for activating the said final protection means at the end of injection step.

Preferably, the automatic activation means comprise second elastic return means connected to the said final protection means intended to urge the said body from the said injection position to the said final protection position.

In an embodiment of the invention, the injection assistance device comprises locking means arranged in such a way as to at least limit the translational movement of the said body with respect to the said final protection means in the final protection position.

In an embodiment of the invention, the injection assistance device comprises control means arranged in such a way as to delimit the said insertion position of the said body.

In an embodiment of the invention, the injection assistance device further comprises automatic-insertion means arranged in such a way as to cause the said body to move axially in the distal direction and to insert the said hollow needle into the injection site.

In an embodiment of the invention, the injection assistance device further comprises retaining means for retaining the said body in the said initial position, the said automatic-insertion means being activated by the release of the said retaining means.

In an embodiment of the invention, the injection assistance device further comprises coupling means arranged in such a way as to move the said piston plunger from the said insertion position to an end-of-injection position and to inject the said product.

In an embodiment of the invention, the injection assistance device further comprises automatic-injection means arranged in such a way as to urge the said coupling means at the end of the insertion step without manual intervention on the part of the user.

In an embodiment of the invention, the injection assistance device comprises maintaining means for keeping the said coupling means in the said insertion position, the said automatic-injection means being activated by the release of the said maintaining means.

In an embodiment of the invention, the injection assistance device further comprises:
  first retaining means of said body in its initial position,
  first deactivating means arranged in such a way as to deactivate said first retaining means and allow the movement of said body to its insertion position,
  actuating means provided with a bearing surface intended to bear on said injection site, said actuating means being able to, under the action of a distal force exerted on said grasping means, move relative to said grasping means from at least a rest position to a bearing position, proximally spaced relative to said rest position, and cause, during this movement, via the first deactivation means, the deactivation of the first retaining means
  protection means intended to receive, at least partially, said body, and being arranged in such a way as to allow the axial mobility of said body relative to said protection means at least from an injection position, in which said needle is exposed, and a protection position, in which said protection means covers at least partially said needle,
  said protection means being coupled to second elastic return means aiming at moving said protection means from said injection position to said protection position,
  second retaining means of said protection means in its injection position,
  second deactivating means arranged in such a way as to be able to deactivate said second retaining means and authorize the movement of said protection means from its injection position to its protection position.

Preferably, the second deactivating means are designed to deactivate said second retaining means under release of said distal force exerted on said grasping means against the injection site.

In an embodiment of the invention, the second deactivating means are designed to deactivate said second retaining means under additional distal pressure applied on the coupling means at the end of the injection step.

In an embodiment of the invention, the injection assistance device further comprises at least:
  locking means of said second deactivating means, arranged in such a way as to prevent the triggering of said second deactivating means in the injection position, at least part of said locking means being movable within said actuating means from a locked position to an unlocked position,
  releasing means arranged in such a way as to release said locking means under the effect of a manual force exerted on said coupling means at the end of injection step,
  second elastic return means aiming at moving part of said locking means from its locked position to its unlocked position.

The present invention also relates to an injection set for injecting a product into an injection site, the said injection set comprising at least:
  an injection device comprising at least:
    a hollow body intended to receive a product that is to be injected, the said body being equipped with a hollow injection needle intended, during a first phase known as the insertion phase, to penetrate an injection site and, during a second phase known as the injection phase, to channel the said product from the said body towards the said injection site, at least one piston plunger housed in a more or less sealed manner in the said body and intended to be moved in the distal direction by movement means in the said injection phase during which it drives the said product through the said needle, characterized in that it comprises at least an injection assistance device for assisting with the injection device as described hereinabove.

In one embodiment of the invention, the injection set is in the form of a kit that can be assembled prior to use.

Figure 13:
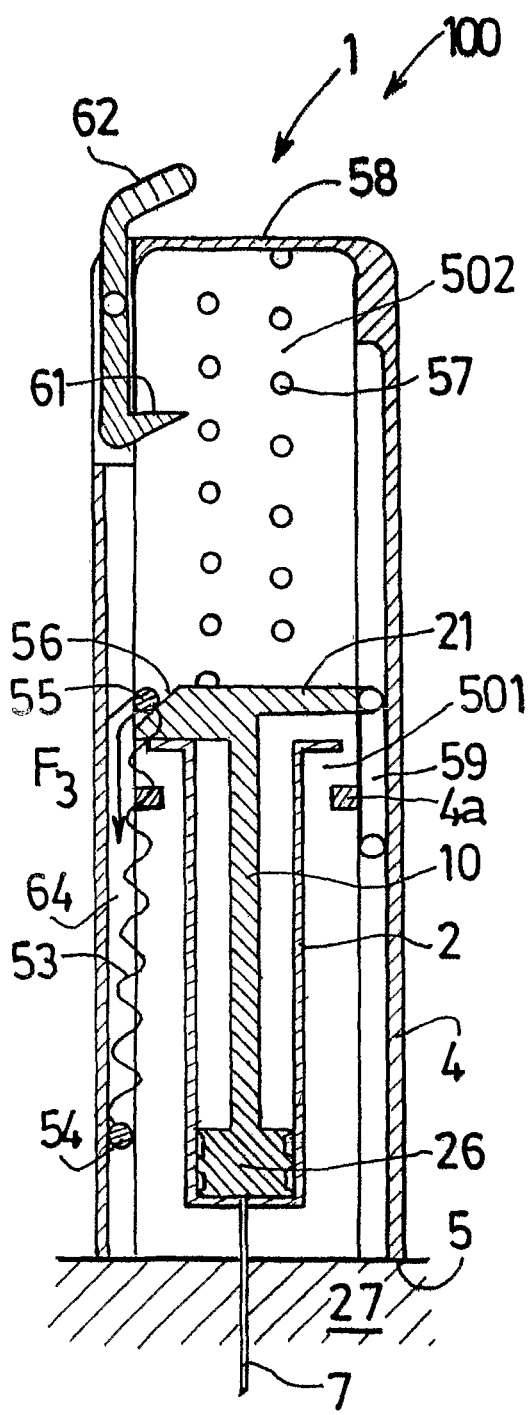
Figure 14:
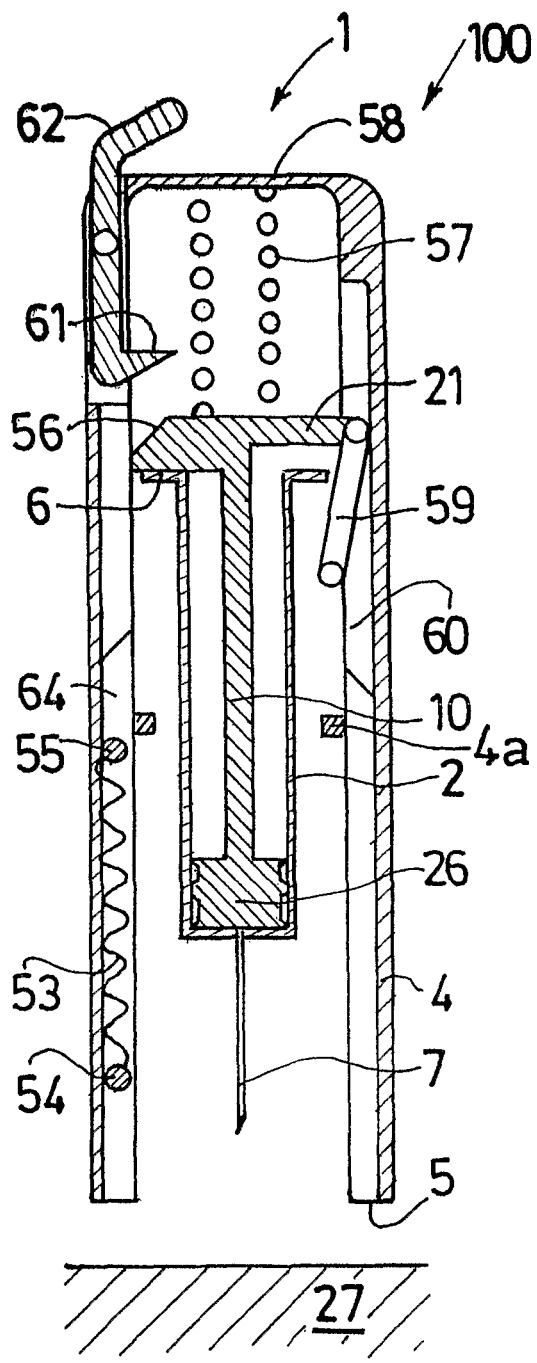
Figure 15:
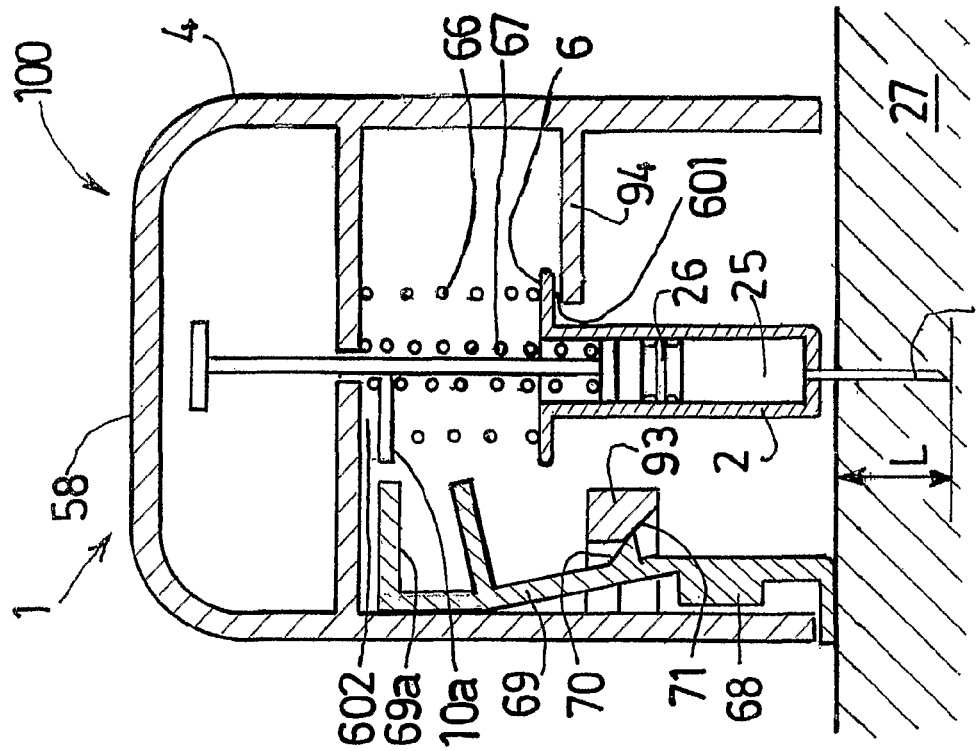
Figure 16:
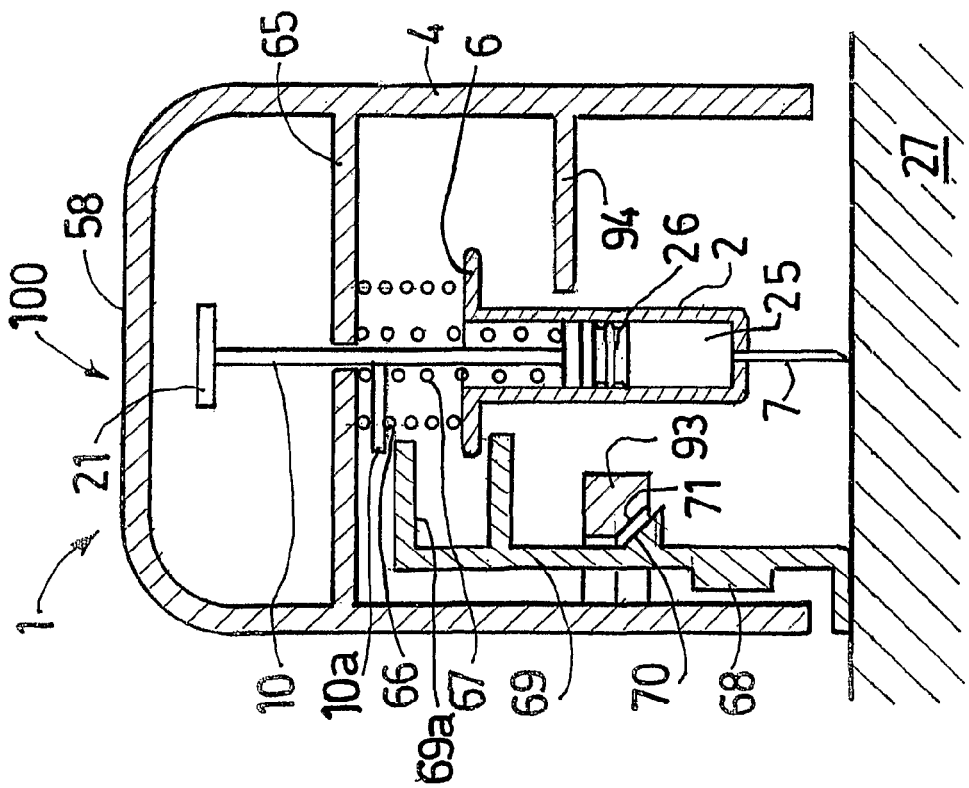
Figure 17:
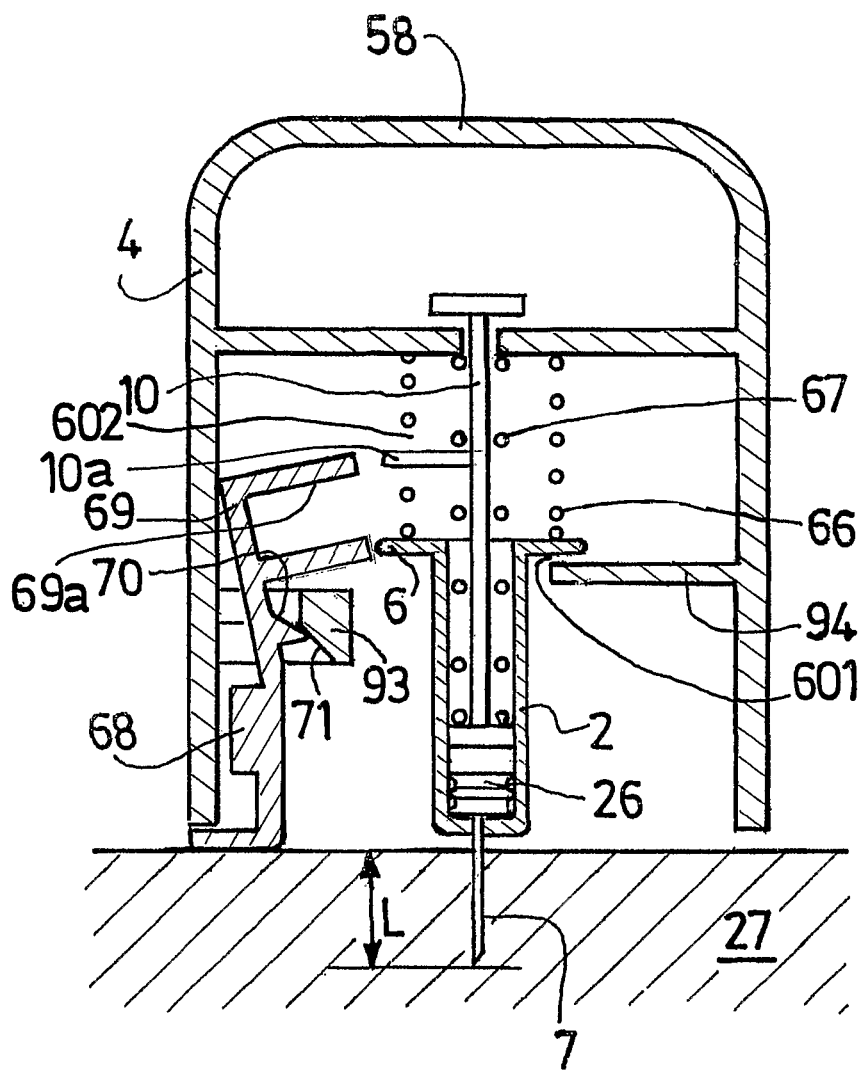
Figure 28:
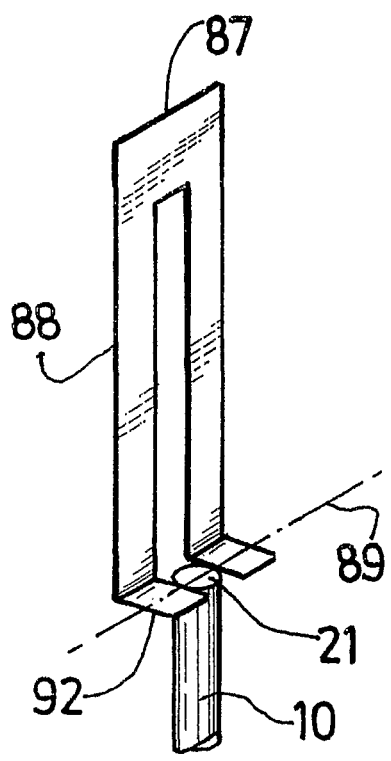
Figure 29:
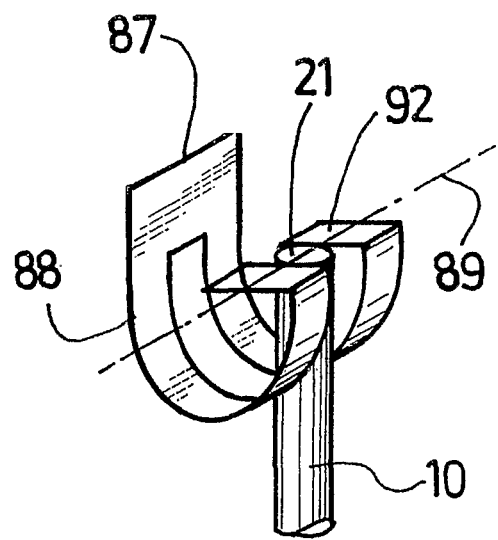
Figure 30:
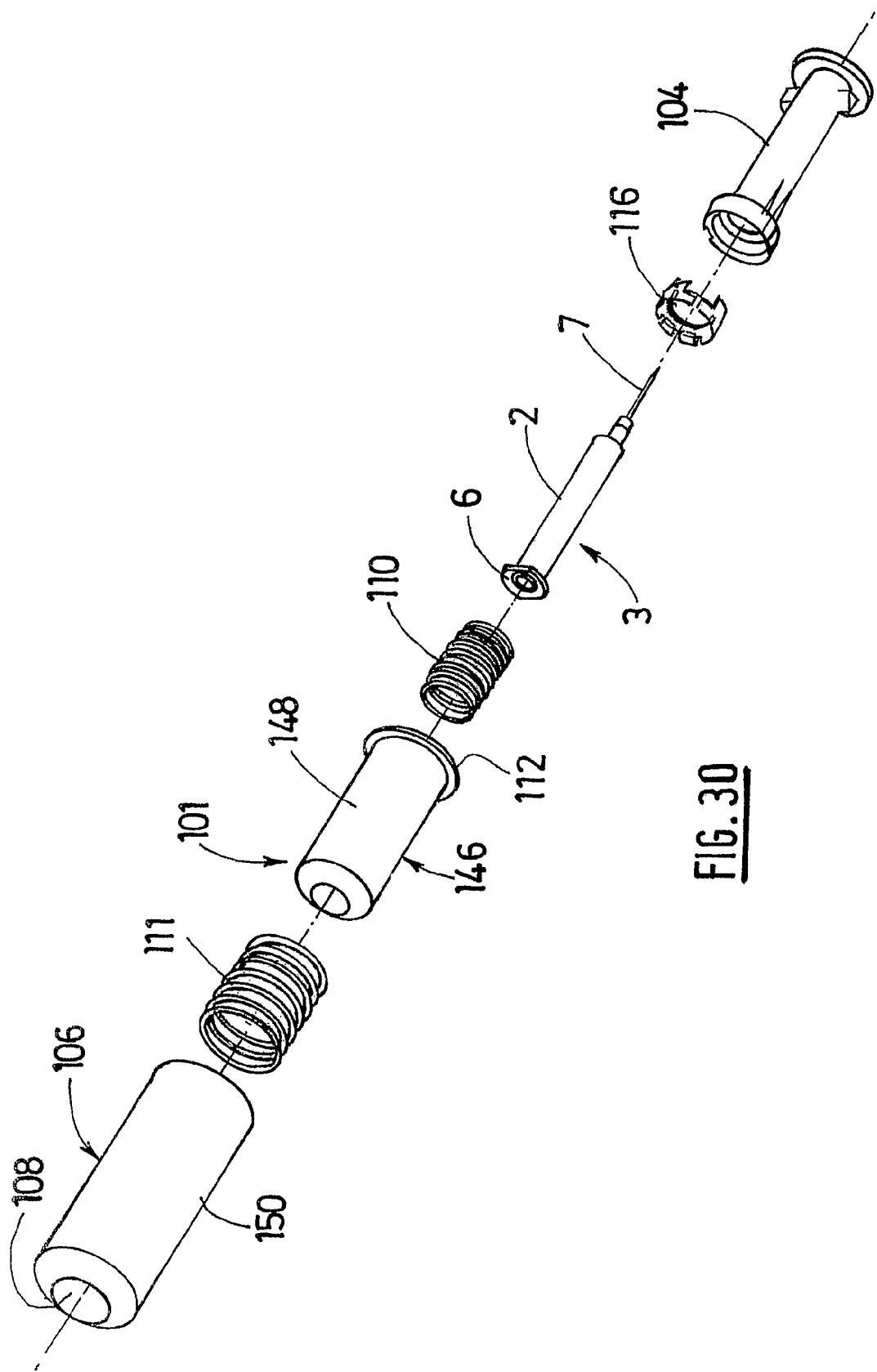
Figure 39:
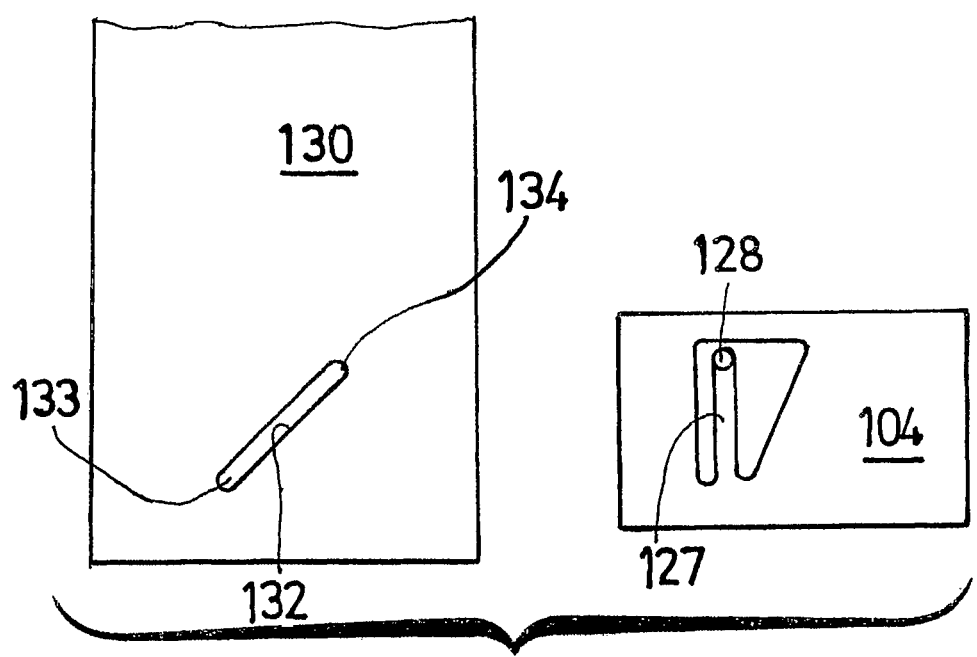
Figures 48, 49:
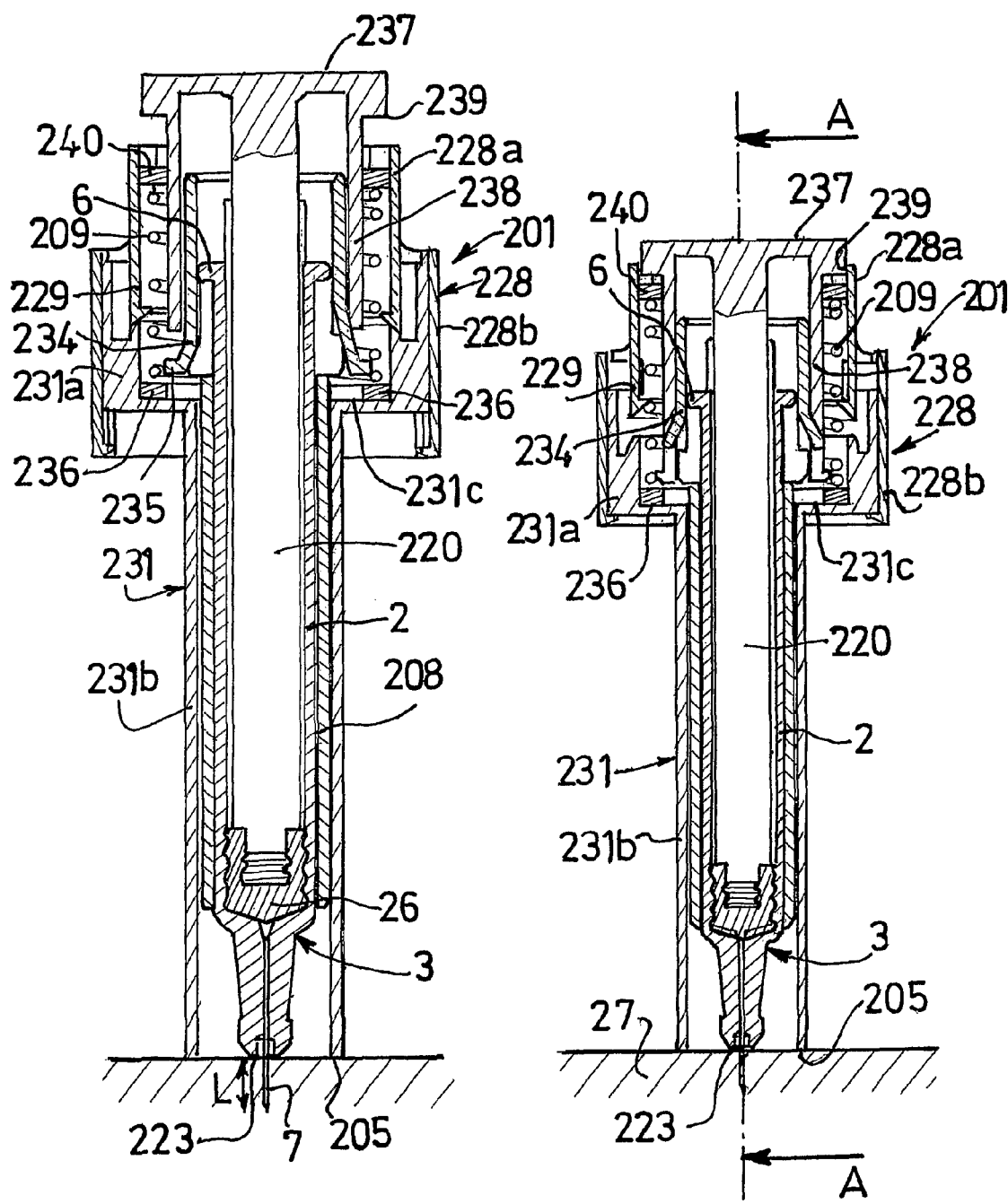
Figures 50, 51:
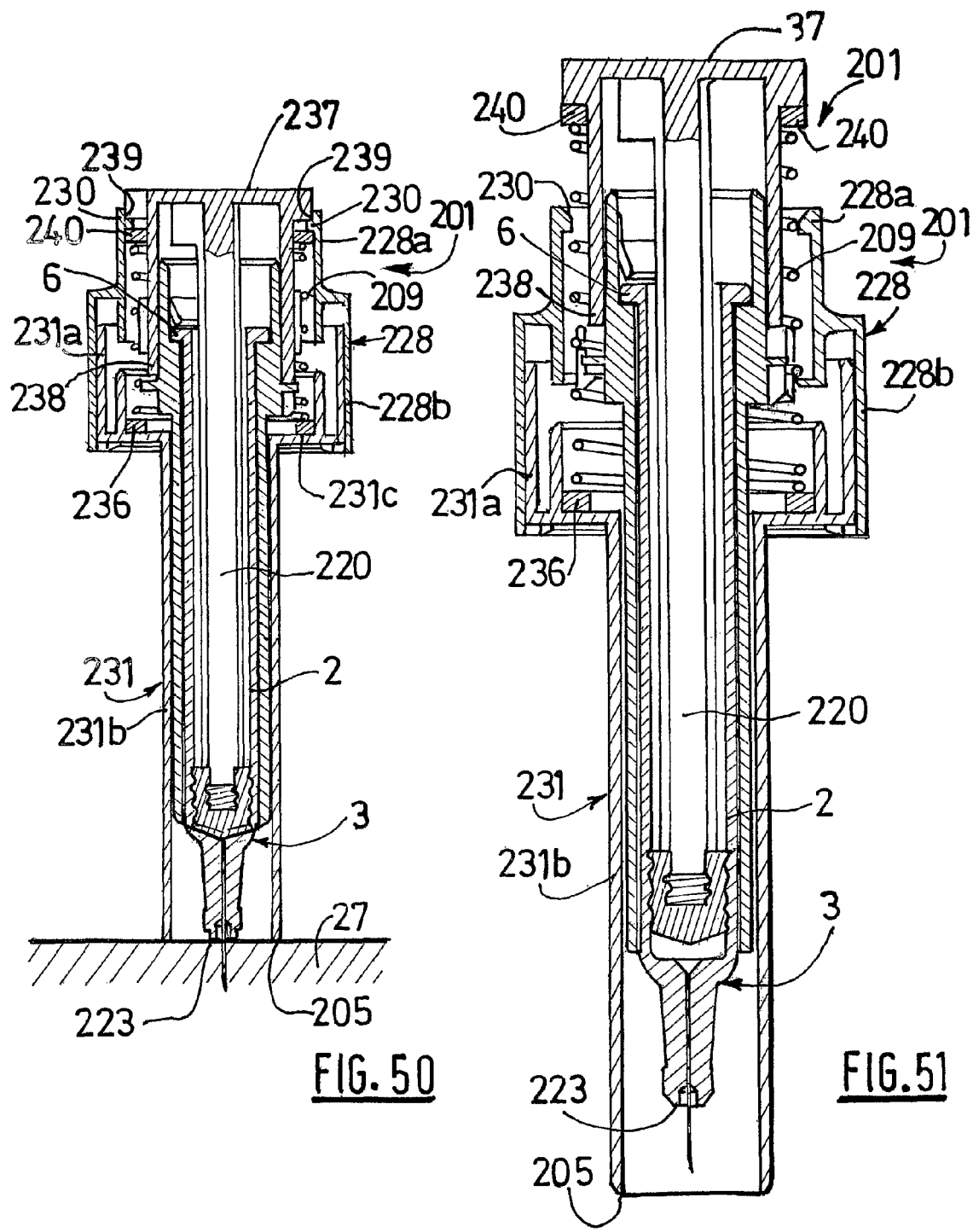

Other advantages and alternative forms of the present invention will be specified with the aid of the description which will follow and of the attached drawings in which:

FIG. 1 is an exploded perspective view of an injection set according to the invention, FIGS. 2 to 5 are simplified sectioned views of the injection set of FIG. 1 in the following respective positions: initial, insertion, end-of-injection and final protection, FIGS. 6 to 10 are sectioned views of a first alternative form of embodiment of an injection set according to the invention in the following respective positions: initial, insertion, end-of-injection before triggering of safety, triggering of safety and final protection, FIGS. 11 to 14 are sectioned views of a second alternative form of embodiment of an injection set according to the invention, in the following respective positions: initial, insertion, end-of-injection and final protection, FIGS. 15 to 17 are sectioned views of a third alternative form of embodiment of an injection set according to the invention in the following respective positions: initial, insertion and end-of-injection, FIGS. 18 to 22 are sectioned views of a fourth alternative form of embodiment of an injection set according to the invention in the following respective positions: initial, pre-insertion, insertion and start-of-injection, end-of-injection and final protection, FIGS. 23 to 27 are sectioned views of a fifth alternative form of embodiment of an injection set according to the invention in the following respective positions: initial, insertion, during injection, end-of-injection and final protection, FIGS. 28 to 29 are partial perspective views of the assistance device of FIGS. 23 to 27, FIG. 30 is an exploded perspective view of a sixth alternative form of embodiment of an injection set according to the invention, FIGS. 31 to 34 are sectioned views of the injection set of FIG. 30 in the following respective positions: initial, needle insertion, end-of-injection and final protection, FIGS. 35 to 38 are sectioned views of a seventh alternative form of embodiment of the injection set according to the invention depicted respectively in the following positions: initial, needle insertion, end-of-injection, and final protection, FIG. 39 is a detailed exterior view of the means of locking the injection set of FIGS. 35 to 38 in the final protection position, FIGS. 40 to 45 are side cross section views of an eigth alternative embodiment of an injection set according to the invention depicted in the following positions: before use, after deshielding and before insertion, before insertion during the deactivation of the first retaining means, insertion position, insertion position during the deactivation of the second retaining means, protection position, FIGS. 46 to 49 are side cross section views of a ninth alternative embodiment of an injection set according to the invention depicted in the following positions: before use, insertion position, insertion position during the release of the locking means, insertion position during the deactivation of the second retaining means, FIG. 50 is a cross section view of FIG. 49 along line AA, FIG. 51 is a cross section view of the device of FIG. 46 in the protection position.

In order to make the invention easier to understand, the injection assistance device is described assembled with an injection device with which it forms an injection set.

FIG. 1 depicts an injection set 100 according to the invention, comprising an injection assistance device 1 for an injection device 3, this injection device 3 comprising a hollow body 2 intended to receive a product 25 that is to be injected, at least one hollow injection needle 7 intended to penetrate the injection site 27, and at least one piston plunger 26 housed in the said body 2, the said body 2 and the said piston plunger 26 being able to be moved in axial translation one relative to the other as will be visible from FIGS. 2 to 5. The body 2 also comprises a flange 6 at its proximal end.

Figure 2:
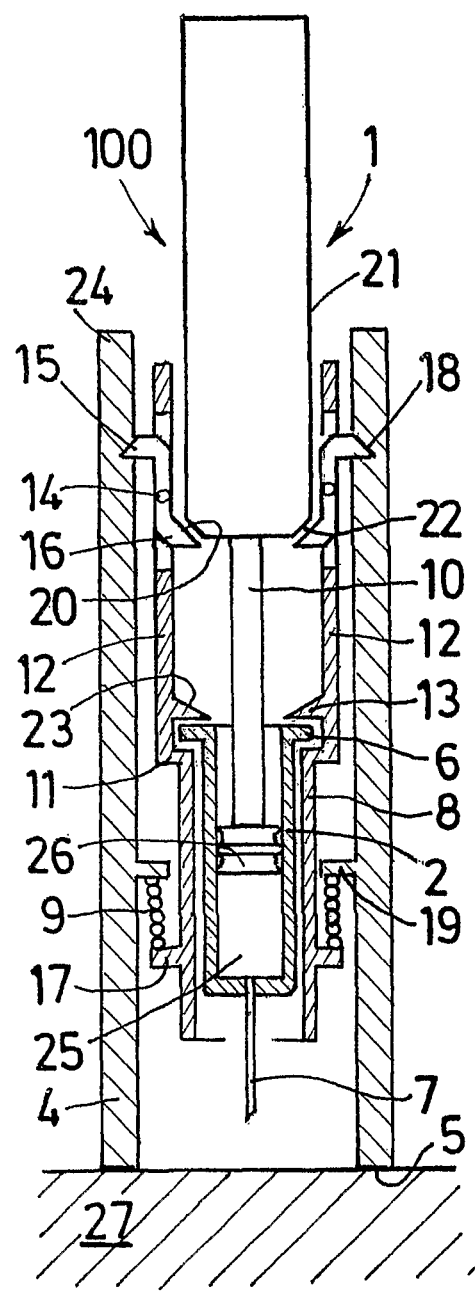
Figure 3:
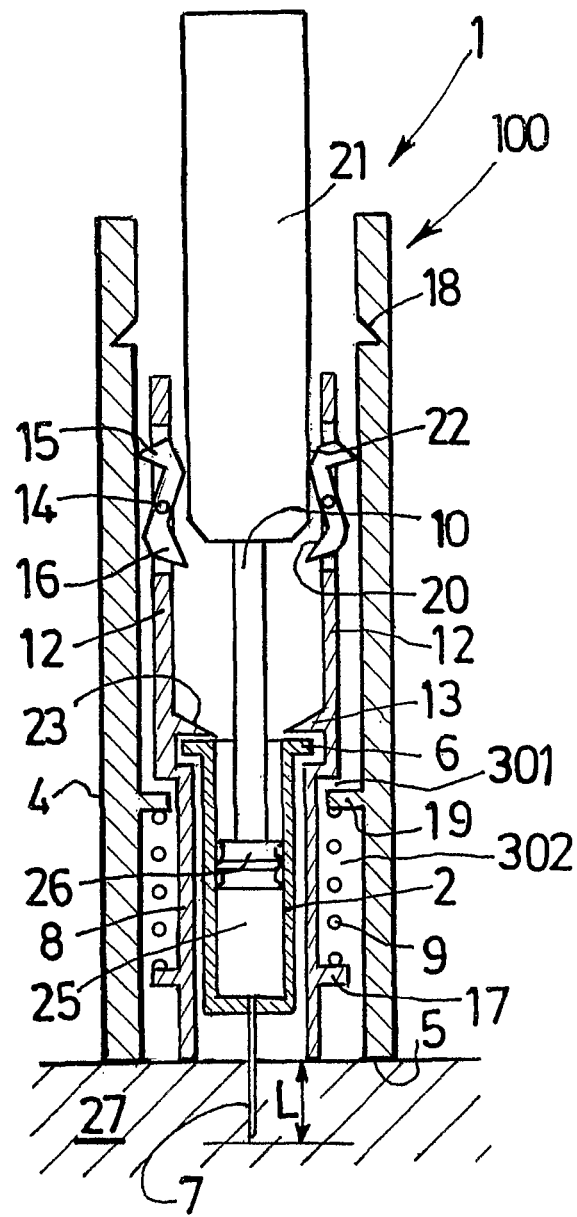
Figure 4:
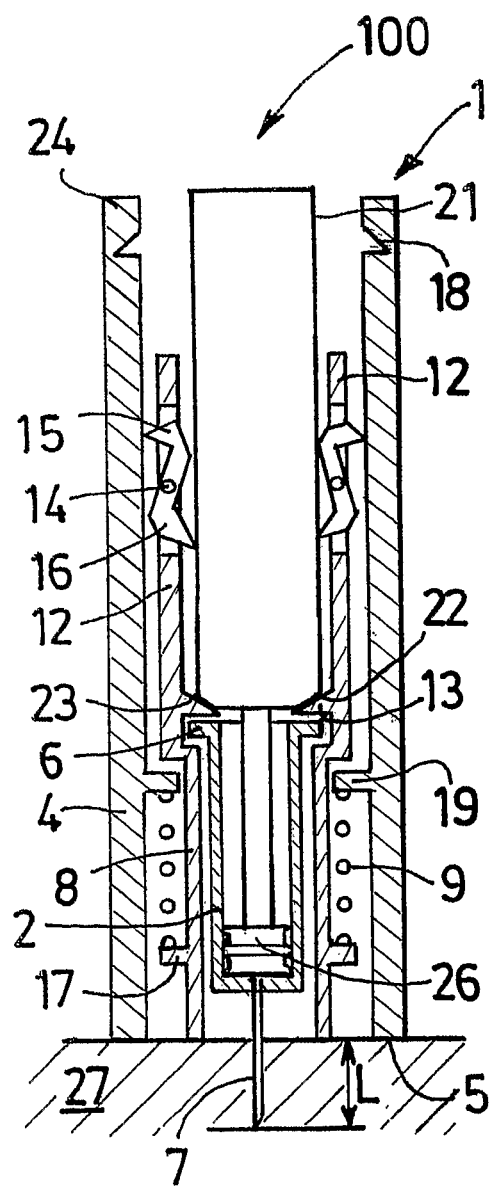

The injection assistance device 1 of FIGS. 1 to 5 comprises a hollow sleeve 4 which at least partially houses the said body 2, this sleeve 4 being provided with at least one bearing surface 5 intended to come into contact with the surface of the injection site 27 as shown in FIGS. 2 to 4.

The injection assistance device 1 also comprises an intermediate ring 8 attached to the flange 6 of the body 2, a spring 9, arranged between the said sleeve 4 and the said intermediate ring 8, and a plunger rod 10 intended to be coupled to the piston plunger 26 in order to inject the product 25.

The plunger rod 10 is equipped with a head 21 the distal end of which is equipped with an external ramp 22.

At its proximal end the intermediate ring 8 comprises at least an external radial rim 11 from which two diametrically opposed tabs 12 extend in the proximal direction, each tab 12 being equipped on its internal wall and in its distal part with at least one internal radial projection 13 able to deflect radially outwards, each tab 12 further comprising, formed in the wall of its proximal part, at least one tab 14 comprising an external radial proximal tooth 15 and an internal radial distal tooth 16, each of the said proximal 15 and distal 16 teeth being able to deflect radially in such a way that the outwards radial flexing of the said distal tooth 16 causes the inwards radial flexing of the said proximal tooth 15.

The distal tooth 16 is equipped with an inclined proximal face 20. The internal radial projection 13 comprises a sloping proximal face 23.

The intermediate ring 8 further comprises at least one external radial stop 17 formed on the external wall of its distal part.

The sleeve 4 comprises at least one notch 18 formed on the internal wall of its proximal part and an internal radial step 19 situated on the internal wall of its distal part.

As can be seen from FIGS. 2 to 5, the proximal end of the spring 9 bears against the distal face of the said radial step 19 and the distal end of the spring 9 bears against the proximal face of the said radial stop 17.

The injection assistance device 1, into which the injection device 3 is integrated, is supplied in the initial position shown in FIG. 2. In this position, the flange 6 of the body 2 is clipped between the said external radial rim 11 and the said internal radial projection 13. The spring 9 is compressed and the said proximal tooth 15 is engaged in the said notch 18 so as to block the translational movement of the said intermediate ring 8 with respect to the said sleeve 4. The sleeve 4 entirely covers the hollow needle 7 and the injection assistance device 1 is therefore completely safe.

In order to proceed with the injection, the user grasps hold of the sleeve 4 via a proximal region for holding 24 and places it bearing, via its bearing surface 5, against the surface of the injection site 27.

The user then engages the plunger rod 10 inside the sleeve 4 in the axial direction. During this movement, the said external ramp 22 comes into contact with the said inclined proximal face 20 causing the said distal tooth 16 to flex outwards and therefore causing the said proximal tooth 15 to flex inwards, the said proximal tooth 15 disengaging from the said notch 18 and releasing the said intermediate ring 8 which is moved in the distal direction by the deployment of the said spring 9. As the intermediate ring 8 is also fixed to the said collar 6, it carries with it the said body 2 and therefore the said needle 7 which penetrates the injection site 27 as shown in FIG. 3.

Thus, insertion of the needle 7 into the injection site 27 is performed automatically, without the user having to move the said body 2 by hand.

As can be seen from FIG. 3, the needle 7 has penetrated the injection site 27 to a predetermined insertion length L controlled by the distal end of the said intermediate ring 8 coming into abutment against the surface of the injection site 27 and the thrusting of the said spring 9 in the partially expanded state against the said radial stop 17. In this insertion position, the axial gap 301 left between the intermediate ring 8 and the sleeve 4 allows the needle 7 to be kept at the insertion depth L even if the user moves the hand holding the sleeve 4 slightly away from the injection site 27.

Actually, if during the injection step, the user, for instance by inadvertence, releases the distal pressure he exerts on the sleeve 4 when applying it on the injection site 27, causing thereby a limited proximal movement of said sleeve 4, then the spring 9, because it is in a partially expanded state and thanks to the presence of the gap 301, is allowed to dampen said proximal movement by expanding a little more and thereby causing the intermediate ring 8 to be urged towards the site injection 27. The body 2 being coupled to said intermediate ring 8, it is also urged towards the injection site 27 and the needle 7 is maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 9, because it is in a partially expanded state and thanks to the presence of the space 302 between the radial step 19 of the sleeve 4 and the radial stop 17 of the intermediate ring 8, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 9 in a partially expanded state.

During the insertion step that has been described, the plunger rod 10 was not release by the retaining means before the body 2. In consequence, there is limited risk that the injection be started before the needle is inserted at the right insertion depth L.

In addition, in an embodiment not depicted, the injection assistance device 1 can be arranged in order to allow sequential displacement of, in a first step the body 2 and the plunger rod 10 relative to the sleeve 4 and in a second step of the plunger rod 10 relative to said body 2. To do so, internal radial distal teeth 16 and said proximal 15 teeth and said distal 16 teeth are arranged in order to, when the user engages the plunger rod 10 inside the sleeve 4 in the axial direction, first allow the disengagement of the in two separate steps, a first step during which, proximal 15 teeth are disengaged from proximal 15 teeth from notch 18 to allow insertion of the needle 7 with no relative displacement of the plunger rod 10, and a second step in which, when the intermediate ring 8 is in abutment with the injection site 27, the distal 16 teeth are disengaged from the external ramp 22 of the piston rod 10 to allow displacement of the plunger rod 10 relative to the body 2 and allow the injection of the product 25 in the injection site 27. In consequence, there is no risk that the injection be started before the needle is inserted at the right insertion depth L.

In order to actually perform the injection, the user, still keeping the assistance device 1 pressed against the injection site 27, grasps hold of the plunger rod 10 and couples it to the said piston plunger 26 so as to move the said piston plunger 26 in the distal direction. The said piston plunger 26 then drives the product 25 towards the needle 7, and the injection is performed.

At the end of injection, as shown in FIG. 4, the said external ramp 22 comes into contact with the said sloping proximal face 23 and, under the effect of an axial force exerted on the head 21 of the plunger rod 10, causes the said radial projection 13 to flex radially outwards thus disengaging the said flange 6 from the said intermediate ring 8.

Figure 5:
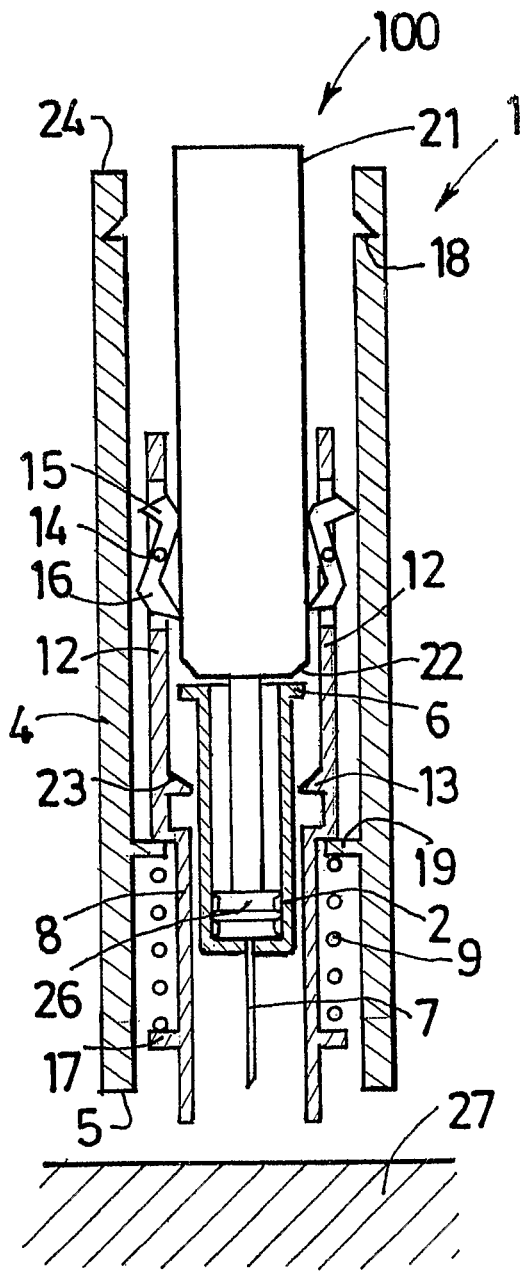

The user then withdraws the injection assistance device 1 from the surface of the injection site 27 and the spring 9, relieved of the pressure exerted on it by the said surface of the said injection site 27, returns to its expanded state, carrying with it the said intermediate ring 8, of which the distal part covers the needle 7 as shown in FIG. 5.

The said radial stop 17 then comes into abutment against the bearing surface 5 of the said sleeve 4, thus locking the translational movement of the said sleeve 4 with respect to the intermediate ring 8.

Thus, the injection assistance device 1 is completely safe and the user can discard it without the risk of needlestick injury.

In an embodiment, not depicted, of the invention, insertion of the needle is triggered by a rotation of the said intermediate ring with respect to the said plunger rod.

FIGS. 6 to 10 illustrate a first alternative form of embodiment of the injection set 100 according to the invention. Identical references have been maintained.

The injection set 100 of FIGS. 6 to 10 comprises an injection assistance device 1 for an injection device 3, this injection device 3 comprising a hollow body 2 intended to receive a product 25 that is to be injected, at least one hollow injection needle 7 intended to penetrate the injection site 27, and at least one piston plunger 26 housed in the said body 2. The body 2 also has a flange 6 at its proximal end.

Figure 6:
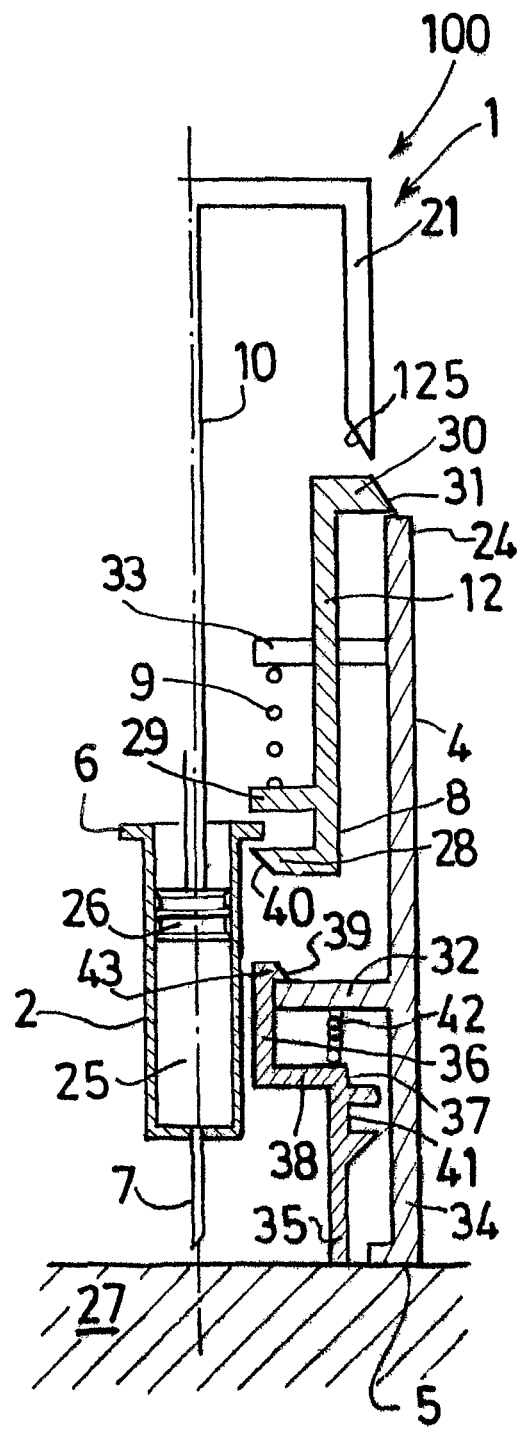
Figure 7:
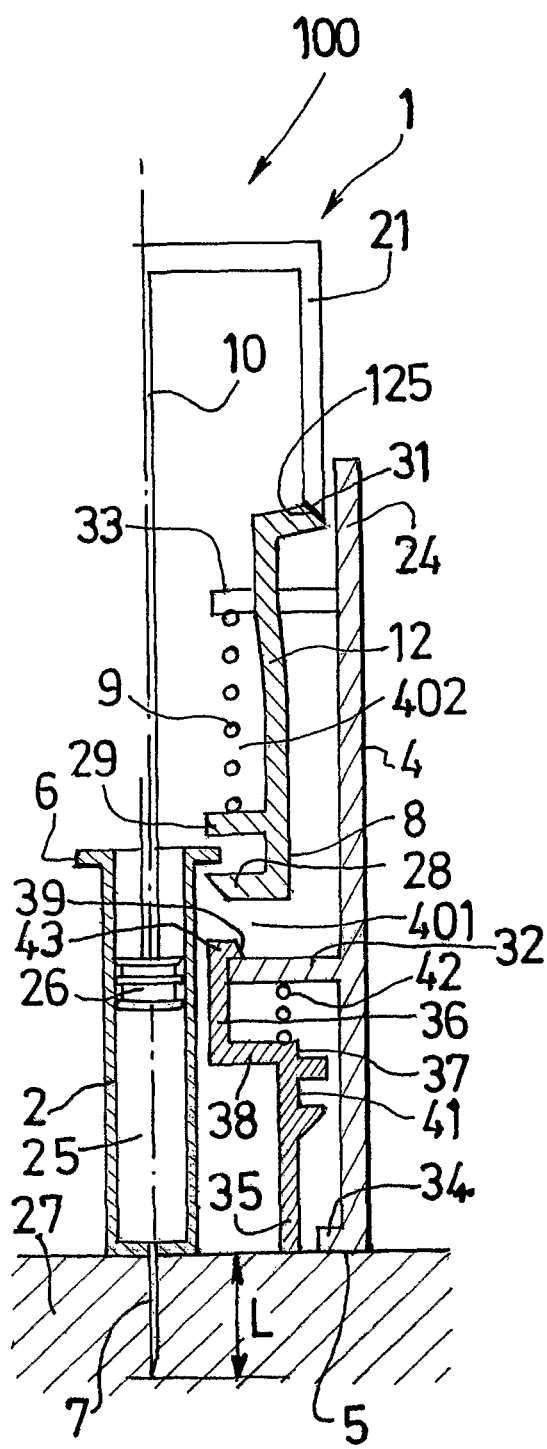

The injection assistance device 1 of FIGS. 6 to 10 comprises a hollow sleeve 4 which at least partially houses the said body 2, this sleeve 4 being provided with at least one bearing surface 5 intended to come into contact with the surface of the injection site 27 as shown in FIGS. 6 to 8.

The injection assistance device 1 also comprises an intermediate ring 8 attached to the flange 6 of the hollow body 2, a first spring 9 arranged between the said sleeve 4 and the said intermediate ring 8, and a plunger rod 10 intended to be coupled to the piston plunger 26 in order to perform the injection.

The plunger rod 10 is equipped with a head 21 forming a longitudinal skirt of which the distal end is equipped with an internal ramp 125.

The said intermediate ring 8 comprises a distal tooth 28, a proximal tooth 29 and at least two diametrically opposed tabs 12 each one extending in the proximal direction from the proximal face of the said proximal tooth 29, each tab 12 being equipped at its proximal end with an external radial projection 30 able to deflect radially inwards. The said external radial projection 30 comprises an inclined proximal face 31. The said distal tooth 28 also comprises an inclined distal face 40.

In FIGS. 6 to 10, the sleeve 4 comprises a proximal part and a distal part separated from one another by an internal radial rim 32. The proximal part of the said sleeve 4 is equipped with an internal radial stop 33 and the distal part of the said sleeve 4 is equipped with an internal bulge 34.

In its distal part, the said sleeve 4 accommodates a sheath 35 comprising a tubular proximal part 36 and a tubular distal part 37, the diameter of the cross section of the proximal part 36 being smaller than the diameter of the cross section of the distal part 37, the said proximal 36 and distal 37 parts being connected to one another by a transverse wall 38 in the form of a circular band, the said proximal part 36 being equipped at its proximal end with an external radial step 43 able to deflect radially inwards. The said external radial step 43 is equipped with a sloping proximal face 39. The said sheath 35 also comprises a slot 41 formed on the external wall of its tubular distal part 37.

The injection assistance device 1 of FIGS. 6 to 10 also comprises a second spring 42 arranged between the said sheath 35 and the distal part of the said sleeve 4.

In the initial position depicted in FIG. 6, the said first spring 9 is in the compressed state and its distal end bears against the proximal face of the said proximal tooth 29, while its proximal end bears against the distal face of the said radial stop 33. In this position, the said second spring 42 is also in the compressed state and its distal end bears against the proximal face of the said transverse wall 38 of the said sheath 35 whereas its proximal end bears against the distal face of the said internal radial rim 32.

The intermediate ring 8 is clipped onto the flange 6 of the hollow body 2 by means of its distal 28 and proximal 29 teeth. The said external radial projection 30 is in abutment against the proximal end 24 of the said sleeve 4, blocking the translational movement of the said body 2 with respect to the said sleeve 4. The distal face of the said radial step 39 is in abutment against the proximal face of the said radial rim 32, blocking the translational movement of the said sleeve 4 with respect to the said sheath 35.

In the initial position depicted in FIG. 6, the said sleeve 4 and the said sheath 35 completely cover the needle 7. The injection assistance device 1 is therefore completely safe.

In order to proceed with the administering of the product 25, the user grasps hold of the sleeve 4 via its proximal end 24, forming a proximal region for holding of the said sleeve 4, and places it bearing, via its bearing surface 5, against the surface of the injection site 27.

The user then engages the plunger rod 10 inside the sleeve 4 in the distal direction. During this movement, the said internal ramp 125 comes into contact with the said inclined proximal face 31 causing the said external radial projection 30 to flex and disengage from the said sleeve 4 and release the said intermediate ring 8, the latter being moved in the distal direction, by the deployment of the said first spring 9 which returns to a partially expanded state. As the intermediate ring 8 is also fixed to the said flange 6, it carries with it the said hollow body 2 and therefore the said needle 7 which penetrates the injection site 27 as shown in FIG. 7.

As can be seen in FIG. 7, the needle 7 has penetrated the injection site 27 to a predetermined insertion length L controlled by the distal face of the said intermediate ring 8 coming into abutment against the proximal face of the said radial rim 32 and by the thrusting of the said first spring 9 in the partially expanded state against the proximal face of the proximal tooth 29 of the said intermediate ring 8.

In the insertion position shown on FIG. 7, a gap 401 is left between the distal tooth 28 of the intermediate ring 8 and the internal radial rim 32 of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 9, because it is in a partially expanded state and thanks to the presence of the gap 401, is allowed to dampen said proximal movement by expanding a little more and thereby causing the intermediate ring 8 to be urged towards the site injection 27. The body 2 being coupled to said intermediate ring 8, it is also urged towards the injection site 27 and the needle 7 is maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 9, because it is in a partially expanded state and thanks to the presence of the space 402 between the radial stop 33 of the sleeve 4 and the proximal tooth 29 of the intermediate ring 8, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 9 in a partially expanded state.

During the insertion step that has been described, the intermediate ring 8 is forming a spacer that rigidly connects, during the insertion step, the plunger rod 10 to the body 2. There is therefore no risk that the injection be started before the needle 7 is inserted at the right insertion depth L.

In order to actually administer the product 25, the user, still holding the injection assistance device 1 against the injection site 27, grasps hold of the plunger rod 10 and moves it in the distal direction. During this movement, the said internal ramp 125 in contact with the said inclined proximal face 31 causes the said external radial projection 30 to flex and disengage from the said head 21 of the plunger rod 10, enabling the distal displacement of the piston plunger relative to said body 2. The said piston plunger 26 then drives the product 25 towards the needle 7 and the injection is administered, until the piston plunger 26 comes in abutment with the distal end of the body 2, as shown on FIG. 8.

Once the injection is completed, under the effect of the axial pressure exerted on the said intermediate ring 8 by the said first spring 9, the said inclined distal face 40 of the said distal tooth 28 comes into abutment against the said sloping proximal face 39 of the said external radial step 43 and causes the inwards radial flexing of the said external radial step 43 which disengages the said sheath 35 from the said sleeve 4, as shown on FIG. 9.

Figure 10:
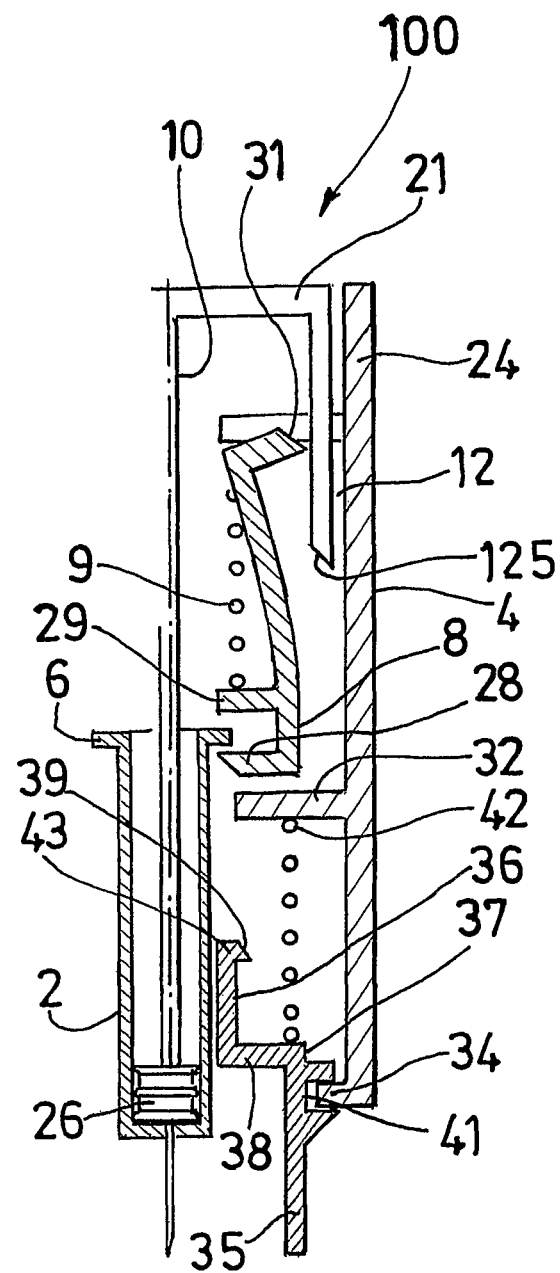

The user then withdraws the injection assistance device 1 from the surface of the injection site 27 and the second spring 42, relieved of the pressure exerted on it by the said surface of the said injection site 27 via the distal part 37 and the transverse wall 38 of the said sheath 35, returns to its expanded state, carrying with it the said sheath 35 which covers the needle 7 as shown in FIG. 10.

As the said second spring 42 deploys, the said bulge 34 of the said sleeve 4 is engaged in the said slot 41 of the said sheath 35, thus locking the translational movement of the said sleeve 4 with respect to the said sheath 35.

Thus, the injection assistance device 1 is completely safe and the user can discard it without the risk of needlestick injury.

FIGS. 11 to 29 depict a second alternative forms of embodiment of the injection set 100 according to the invention which also comprise automatic injection means.

FIGS. 11 to 14 relate to a first of its alternative forms. In these figures, the injection assistance device 1 according to the invention comprises a first spring 53 arranged between the said hollow body 2 and the said sleeve 4. The distal end 54 of the said first spring 53 is fixed to the internal wall of the distal part of the said sleeve 4. The proximal end 55 of the said first spring 53 bears against an inclined distal face 56 of the said head 21 of the plunger rod 10. The sleeve 4 is provided on its internal walls with a radial stop 4a.

The injection assistance device 1 also comprises a second spring 57 arranged between the said head 21 of the plunger rod 10 and the distal face of the proximal region for holding 58 of the said sleeve 4.

Figure 12:
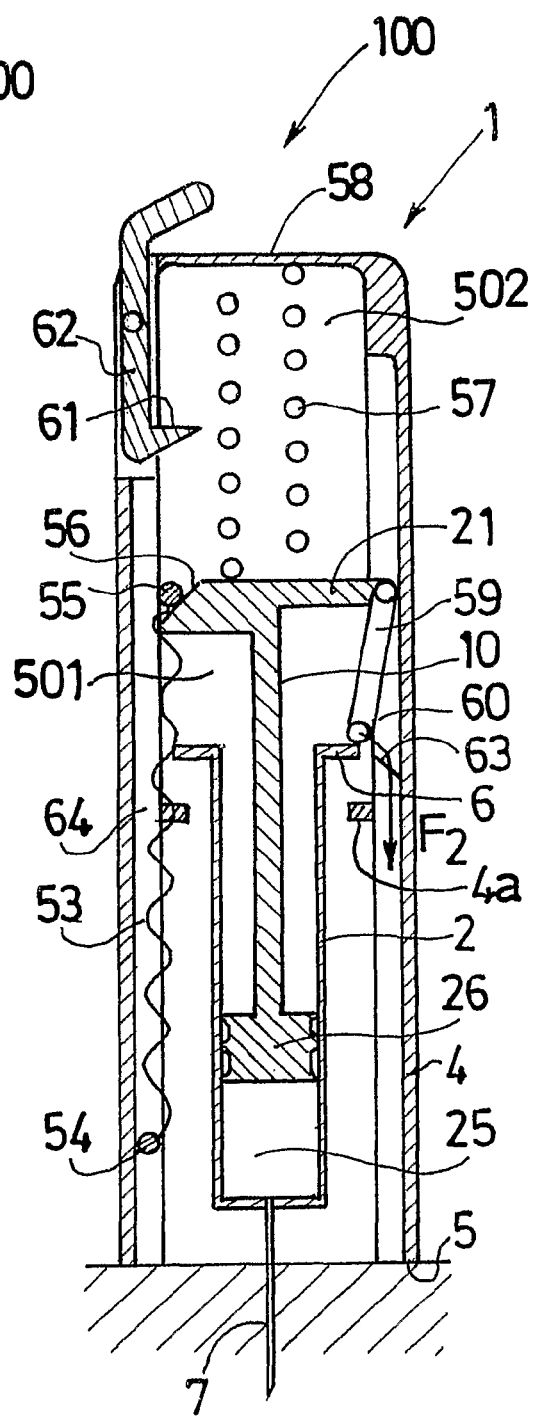

The head 21 of the plunger rod 10 comprises a longitudinal tab 59, extending in the distal direction, able to deflect outwards and engaging the said head 21 of the plunger rod 10 and the said flange 6, as depicted in FIG. 13. In FIGS. 11 to 14, this longitudinal tab 59 is in the form of an articulated arm comprising a window (not depicted) able to collaborate with a long bulge 60 formed on the proximal part of the internal wall of the said sleeve 4.

Figure 11:
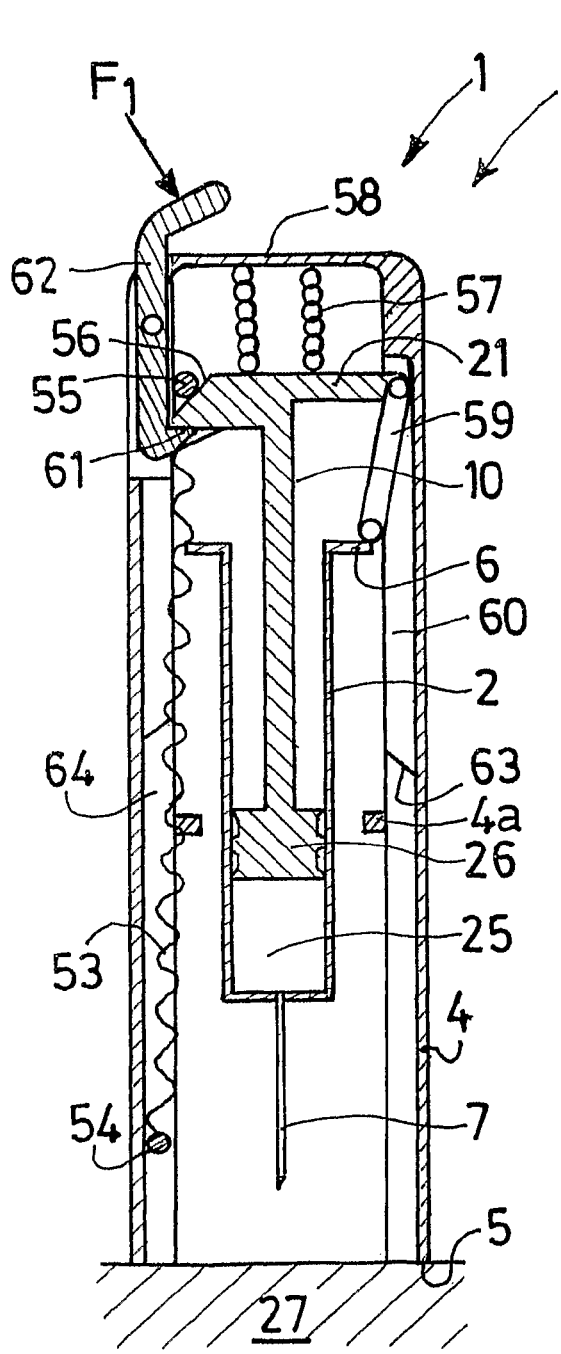

In the initial position, as depicted in FIG. 11, the said first spring 53 is in the stretched-out state. It is kept in this stretched-out state by a bearing surface 61 coupled to a button 62 situated on the external wall of the said sleeve 4, the said bearing surface 61 being able to deflect outwards and to release the said first spring 53 via pressure exerted on the said button 62.

The said second spring 52 is in the state of rest.

The plunger rod 10 is separated from the body 2 by an articulated arm 59 which, in the insertion step, as described below, will form spacer means preventing the plunger rod 10 from moving relative to said body 2.

Once the user has grasped the injection set 100 by the sleeve 4 and has brought said sleeve 4 to bear against the surface of the injection site 27, the user presses on the button 62 in the direction of the arrow F1 depicted in FIG. 11 to deflect the said bearing surface 61 and release the said first spring 53 which, on returning to a compressed state, drives the said head 21 of the plunger rod 10 in the distal direction. As the said head 21 of the plunger rod 10 is rigidly connected to the said flange 6 by the articulated arm 59, it is the assembly comprising the plunger rod 10 and the hollow body 2, and therefore the needle 7, which is moved in the distal direction, the said movement automatically inserting the said needle 7, as shown in FIG. 12.

During this movement, the said second spring 57, the distal end of which is fixed to the proximal face of the said head 21 of the plunger rod 10, has been stretched out, as shown in FIG. 12, and is therefore in a partially expanded state.

At the end of the insertion position, the said articulated arm 59 reaches the distal end 63 of the said bulge 60 and is deflected outwards, disengaging the said head 21 of the plunger rod 10 from the said flange 6, as shown by the arrow F2 in FIG. 12.

The said first spring 53 continues its return to its state of rest and carries with it the said head 21 of the plunger rod 10 which, free to move in the translational movement with respect to the said flange 6 and therefore with respect to the said hollow body 2, drives the said piston plunger 26 in the distal direction and administers the product 25. Thus, the injection is performed automatically without the user having to intervene.

During the injection step, the said second spring 57 is continued to be stretched out under the action of the said first spring 53.

As can be seen from FIGS. 12 and 13, a gap 501 is left between the flange of the body 2 and the radial stop 4a of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 57, because it is in a partially expanded state and thanks to the presence of the gap 501, is allowed to dampen said proximal movement by expanding a little more and thereby causing the head 21 of the plunger rod 10, and by consequence the body 2, to be urged towards the site injection 27. The needle 7 is therefore maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 57, because it is in a partially expanded state and thanks to the presence of the space 502 between the distal face of the proximal region for holding 58 of the sleeve 4 and the head 21 of the plunger rod, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 57 in a partially expanded state.

At the end of the injection position, as shown in FIG. 13, the proximal end 55 of the said first spring 53 disengaged from the inclined distal face 56 of the said head 21 of the plunger rod 10 in the direction of the arrow F3 because this head has arrived opposite a longitudinal depression 64 formed on the distal part of the internal wall of the said sleeve 4. The said first spring 53 therefore no longer exerts any tension on the said second spring 57 which returns to its compressed state of rest and carries with it the assembly comprising the head 21 of the plunger rod 10 and the hollow body 2, returning the said needle 7 to the inside of the said sleeve 4, as shown in FIG. 14.

Thus, in the final protection position as depicted in FIG. 14, the said needle 7 is completely covered and the injection set 100 is safe. It can be discarded without any risk of needlestick injury to the user.

FIGS. 15 to 17 depict a second alternative form of embodiment of the injection set 100 according to the invention, of which the said sleeve 4 comprises a transverse wall 65 against the distal face of which the respective proximal ends of a first spring 66 and of a second spring 67 bear. The distal end of the said first spring 66 bears against the proximal face of the said flange 6. The distal end of the said second spring 67 bears against the said piston plunger 26.

The sleeve 4 is provided on its internal wall with a radial stop 94.

The plunger rod 10 is provided with a radial projection 10*a*.

The said injection assistance device 1 also comprises an intermediate ring 68, the proximal end of which comprises a first tab or laterally mobile tab 69 engaged in the said flange 6 in the initial position, said tab 69 being able to deflect in order to release the said flange 6 and therefore the said hollow body 2 through the collaboration of one 70 of its surfaces with a complementing surface 71 situated on a complementary rim 93 itself situated on the internal wall of the said sleeve 4. The tab 69 comprises a radial rim 69*a*.

In the initial position, as depicted in FIG. 15, the said first and second springs 66, 67 are in the compressed state, the said laterally mobile first tab 69 is engaged in the said flange 6.

The radial rim 69*a* of the tab 69 is engaged in the radial projection 10*a* of the plunger rod 10.

The user grasps the sleeve 4 of the injection assistance device 1 and applies it on the injection site 27. The user then presses on the proximal bearing region 58 to initiate the automatic insertion of the needle 7. This initiation takes place through the said surface 70 of the said deflecting first tab 71, coming into abutment against the said complementary surface 71 of the said sleeve 4 and subsequent deflection of the said tab 69 which releases at the same time the flange 6 and the radial projection 10*a*. The said first spring 66 is then free to return to a partially expanded state, carrying along with it the said flange 6 and therefore the said hollow body 2 and causes the needle 7 to become inserted into the injection site 27, as shown in FIG. 16.

Through deflection of tab 69, the radial rim 69*a* of said tab 69 has been disengaged from the radial projection 10*a* of the plunger rod 10, freeing said plunger rod 10. As the plunger rod 10 is not free to move before the body 2, the risk of inadvertent injection start before reaching the insertion depth L is limited.

The injection is performed automatically thanks to spring 67, without the user having to intervene.

As can be seen from FIGS. 16 and 17, a gap 601 is present between the flange 6 of the body 2 and the radial stop 94 of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 66, because it is in a partially expanded state and thanks to the presence of the gap 601, is allowed to dampen said proximal movement by expanding a little more and thereby causing the body 2, to be urged towards the site injection 27. The needle 7 is therefore maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 66, because it is in a partially expanded state and thanks to the presence of the space 602 between the distal face of the transversal wall 65 of the sleeve 4 and the body 2, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 66 in a partially expanded state.

FIGS. 18 to 29 relate to two alternative forms of embodiment of the injection set 100 according to the invention, in which forms the automatic-injection means are activated when the resultant of the forces of the said first and/or second and/or third return means, the force needed to overcome the stiction of the said piston plunger 26 and the force with which the sleeve 4 bears against the said injection site 27, is directed in the distal direction.

The injection assistance device 1 of FIGS. 18 to 22 comprises a sleeve tube 75 accommodating the said sleeve 4. The injection assistance device 1 also comprises a first spring 76 arranged between the said piston plunger 26 and the proximal face of the proximal region for holding 77 of the said sleeve tube 75. The said injection assistance device 1 also comprises a second spring 78 arranged between the said hollow body 2 and the said sleeve 4.

Figure 18:
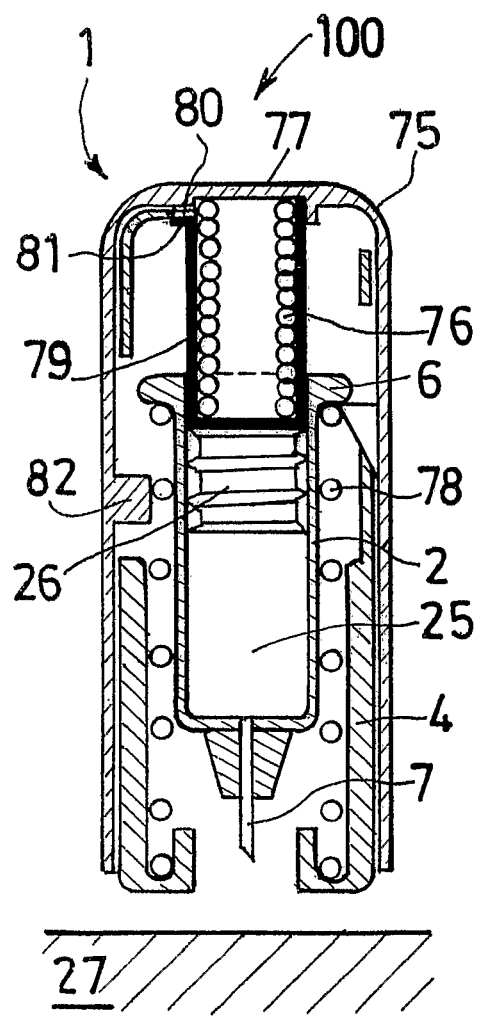

The said first spring 76 is housed within a casing 79, the distal end 80 of which bears, in the initial position as depicted in FIG. 18, against a deflecting tab 81 formed on the internal wall of the said sleeve tube 75. In the initial position, the said first spring 76 is in the compressed state and the said second spring 78 is in the expanded state.

The user grasps the sleeve tube 75 and applies the injection assistance device 1 on the injection site 27.

Figure 19:
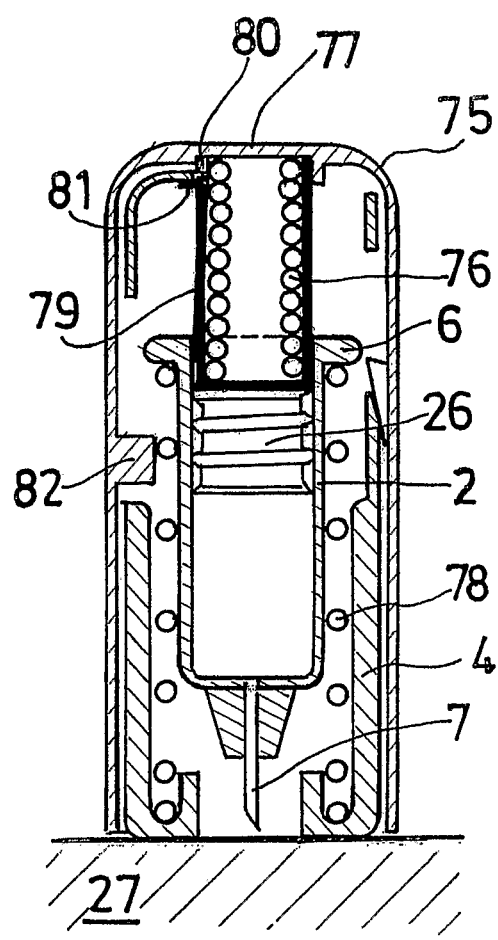

When the user presses against the said proximal region for holding 77 of the said sleeve tube 75, as shown in FIG. 19, the proximal end of the said sleeve 4 deflects the said tab 81 and disengages the said distal end 80 of the said casing 79 and thus releases the said first spring 76 which returns to a partially expanded state, carrying with it, at the same time, the said casing 79 and the said body 2 and causing the said needle 7 to be inserted automatically into the injection site 27, as shown in FIG. 20. While this is happening, the said second spring 78, the proximal end of which bears against the distal face of the said flange 6, is compressed.

As the plunger rod 10 is not free to move before the body 2, the risk of inadvertent injection start before reaching the insertion depth L is limited.

In the end-of-insertion position, the resultant of the forces of the said first and second springs 76, 78, the force needed to overcome the stiction of the said piston plunger 26 and the force with which the said sleeve 4 is pressed against the said injection site 27 is directed in the distal direction and so the said first spring 76 drives the said piston plunger 26 into the said hollow body 2 and administers the injection automatically, as shown in FIG. 21.

As can be seen on FIG. 20, a gap 701 is present between the flange 6 of the body 2 and a radial rim 82 formed on the internal wall of the said sleeve tube 75.

Therefore, if during the injection step, the user, for instance by inadvertence, releases the distal pressure he exerts on the sleeve tube 75 when applying it on the injection site 27, causing thereby a limited proximal movement of said sleeve tube 75, then the first spring 76, because it is in a partially expanded state and thanks to the presence of the gap 701, is allowed to dampen said proximal movement by expanding a little more and thereby causing the body 2, to be urged towards the site injection 27. The needle 7 is therefore maintained at a constant insertion length, namely its predetermined insertion length L.

On the contrary, if during the injection step, the user increases the distal pressure he exerts on the sleeve tube 75 when applying it on the injection site 27, causing thereby a limited distal movement of said sleeve tube 75, then the first spring 76, because it is in a partially expanded state and thanks to the presence of the space 702 between the distal face of the proximal region for holding 77 of the sleeve tube 75 and the piston plunger 26, is allowed to dampen said distal movement by being compressed, thereby maintaining the needle 7 at a constant insertion length, namely its predetermined insertion length L.

The influence of any increase or release of the distal pressure exerted by the user on the sleeve tube 75 during injection step is therefore neutralized by the presence of the spring 76 in a partially expanded state.

At the end of injection, the user withdraws the injection set 100 from the injection site 27 and the said second spring 78, on returning to its expanded state, drives the said sleeve 4 in the distal direction and the needle 7 is covered up again, as shown in FIG. 22. The injection set 100 is therefore completely safe.

The injection assistance device 1 of FIGS. 23 to 29 is a fifth alternative form of embodiment of the injection assistance device 1 of FIGS. 18 to 22 in which the two springs are replaced by a single leaf spring 83. The injection assistance device 1 of FIGS. 23 to 29 comprises no sleeve tube.

The fixed end 84 of the said leaf spring 83 is fixed to the internal wall of the distal part of the said sleeve 4. The moving end 86 of the said leaf spring 83 is held, in the initial position, with the aid of a bearing surface coupled to a button 94 similar to the one described in FIG. 11.

The moving end 86 of the said leaf spring 83 is connected to the proximal end 87 of a deformable moving component 88 of which the distal end 92 is itself linked to the said head 21 of the plunger rod 10 by a pivot connection 89, as shown in FIGS. 28 and 29.

The said moving component 88 is housed in a rail 90 within which it can move translationally, the said rail 90 having the overall shape of a J, namely a first longitudinal part, a curved part and a second longitudinal part shorter than the said first longitudinal part.

In the initial position, as depicted in FIG. 23, the said leaf spring 83 is in the stretched-out state.

The user grasps the sleeve 4 of the injection assistance device 1 and applies it on the injection site 27. By pressing the said button 95, the said leaf spring 83 is released and tries to return to its state of rest. As it does so, its moving end 86 pushes the component 88 along the rail 90, the said moving component 88 driving the said head 21 of the plunger rod 10, the said moving component 88 being in its undeformed configuration as shown in FIG. 28. The said head 21 of the plunger rod 10 itself drives the said body 2 and causes the said needle 7 to be inserted automatically into the injection site 27 as shown in FIG. 24.

At the end of the insertion position, as shown in FIG. 24, the said leaf spring 83 continues its return to its compressed state at rest and the resultant of the forces of the said leaf spring 83, of the force needed to overcome the stiction of the said piston plunger 26, and with which the said sleeve 4 bears against the said injection site 27 is directed in the distal direction and so the said spring 83 drives the said plunger rod 10 which itself drives the said piston plunger 26 into the said hollow body 2 and administers the injection automatically, as shown in FIG. 25.

As can be seen on FIGS. 24 and 25, a gap 801 is present between the flange 6 of the body 2 and a radial rim 91 formed on the internal wall of the sleeve 4.

Therefore, if during the injection step, the user, for instance by inadvertence, releases the distal pressure he exerts on the sleeve 4 when applying it on the injection site 27, causing thereby a limited proximal movement of said sleeve 4, then the spring 83, because it is in a partially expanded state and thanks to the presence of the gap 801, is allowed to dampen said proximal movement by expanding a little more and thereby causing the body 2, to be urged towards the site injection 27. The needle 7 is therefore maintained at a constant insertion length, namely its predetermined insertion length L.

On the contrary, if during the injection step, the user increases the distal pressure he exerts on the sleeve 4 when applying it on the injection site 27, causing thereby a limited distal movement of said sleeve 4, then the spring 83, because it is in a partially expanded state and thanks to the presence of the space 802 between the distal face of the proximal region for holding of the sleeve 4 and the flange 6 of the body 2, is allowed to dampen said distal movement by being compressed, thereby maintaining the needle 7 at a constant insertion length, namely its predetermined insertion length L.

The influence of any increase or release of the distal pressure exerted by the user on the sleeve 4 during injection is therefore neutralized by the presence of the spring 83 in a partially expanded state.

As shown in FIG. 26, the said leaf spring 83 continues its return to its state of rest and the distal end of the said moving component 88 engages in the curved part of the said rail 90 and in so-doing pivots about the pivot connection 89 then rises back up inside the second longitudinal part of the said rail 90 as shown in FIGS. 27 and 29. As the said distal end 92 of the said moving component 88 rises back up inside the said second longitudinal part of the said rail 90, the said moving component 88, via its pivot connection 89, carries along with the said plunger rod 10, as shown in FIG. 29. The said head 21 of the plunger rod 10 itself drives along the said hollow body 2 and therefore the needle 7 which moves up inside the said sleeve 4, as shown in FIG. 27. The injection set 100 is therefore completely safe.

Figure 31:
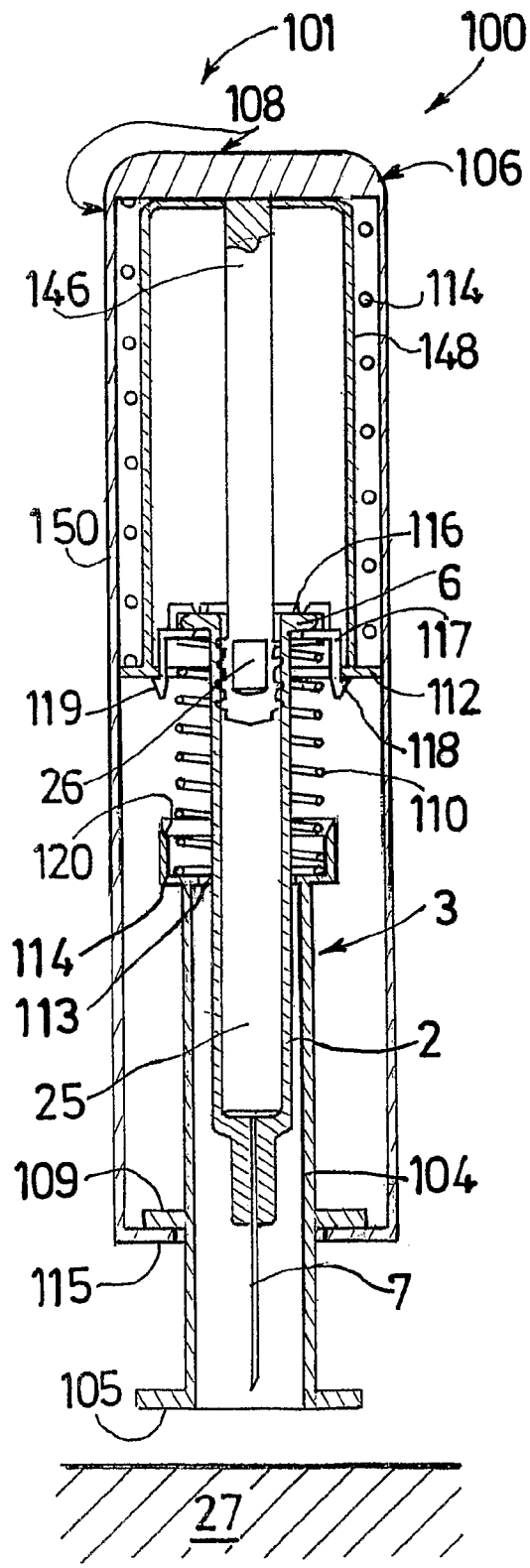
Figure 32:
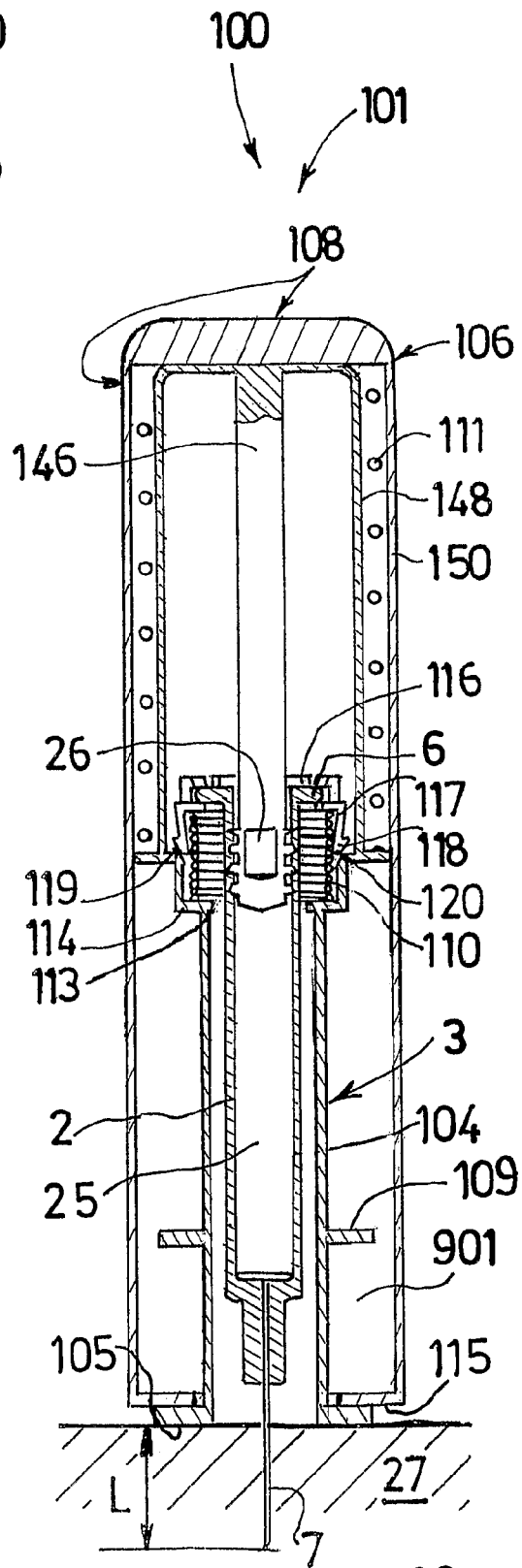

Reference is now made to FIGS. 30 to 34 which depict an injection set 100 according to the invention comprising an injection assistance device 101 for an injection device 3 comprising a body 2, a plunger rod 146, a sleeve 104 and a sleeve tube 106. The sleeve tube 106 defines a longitudinal skirt 150 of which the distal part, in the insertion position as shown in FIG. 32, covers the proximal part of the sleeve 104. The body 2 is intended to receive the product 25 that is to be injected. In the example depicted, this body 2 is equipped at its proximal end with a flange 6. In an alternative form of the invention, not depicted, this flange 6 could be attached to the body 2. In these figures, the body 2 is equipped at its distal end with a hollow injection needle 7 intended to penetrate the injection site 27 to a predetermined insertion depth L.

In FIG. 30, the plunger rod 146 comprises a plunger rod head which is extended in the distal direction by a longitudinal skirt 148 extending in the distal direction. The plunger rod 146 is able to move with respect to the body 2 and is intended to be urged by an axial pressure in the distal direction in order to perform the injection.

Figure 33:
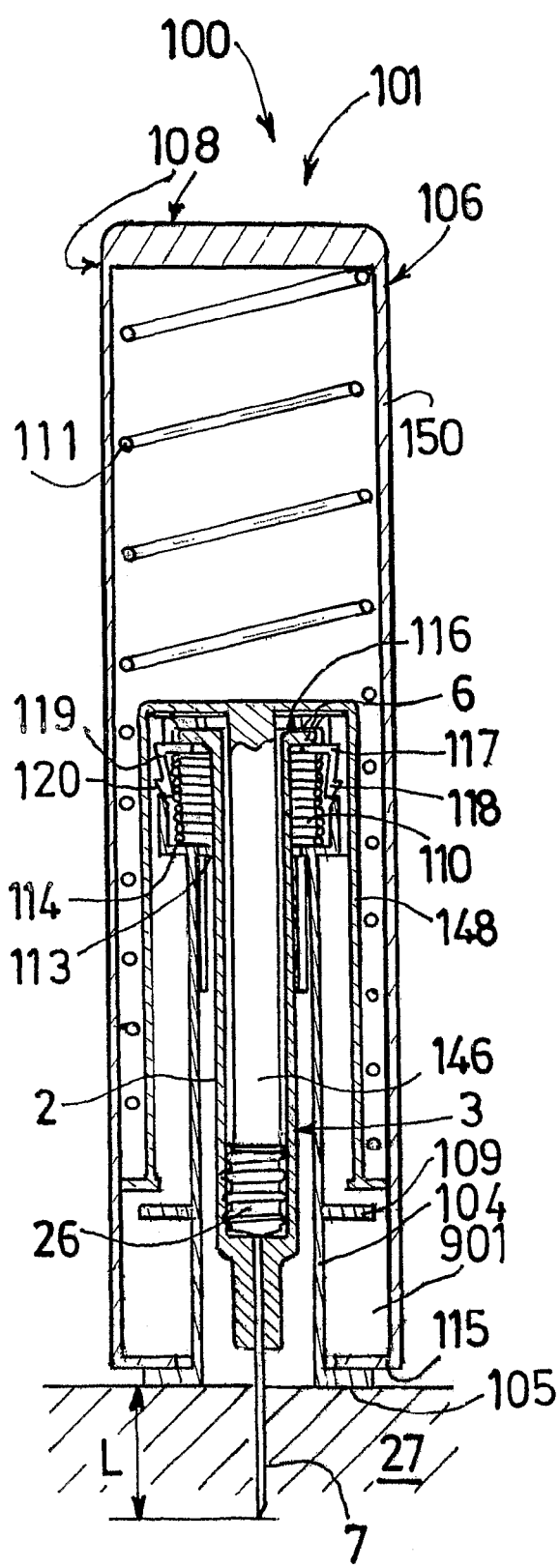
Figure 34:
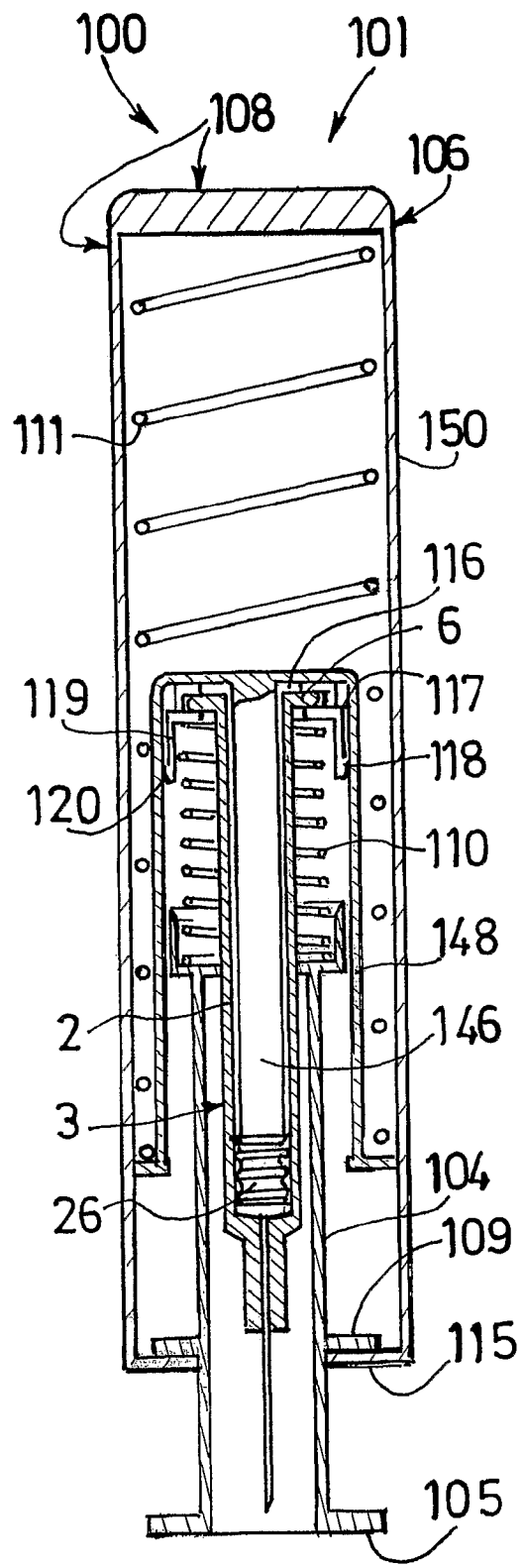

As is apparent from FIGS. 31 to 34, the sleeve 104 houses the body 2 and is able to move with respect to this body 2 between an insertion position (FIGS. 32 and 33) in which the needle 7 is exposed and a final protection position in which the sleeve 104 entirely covers the needle 7 (see FIG. 34).

In FIG. 30, the injection assistance device 101 further comprises a first spring 110 arranged between the body 2 and the said sleeve 104, and a second spring 111 arranged between the longitudinal skirt 148 of the said plunger rod 146 and the sleeve tube 106.

In the example depicted, the distal end of the longitudinal skirt 148 of the said plunger rod 146 is equipped with an exterior radial rim 112. This rim 112 may be in the form of a continuous or discontinuous annular bulge. The sleeve 104 comprises a radial stop 113 situated on its internal wall, as can be seen in FIG. 31. This radial stop 113 may be in the form of a continuous or discontinuous annular bulge. The sleeve 104 at its distal end comprises an external radial step 114. This step 114 may be in the form of a continuous or discontinuous annular bulge. The proximal end of the sleeve 104 is equipped with an internal ramp 120. The distal end of the sleeve 104 is equipped with a bearing surface 105 designed to be placed in contact with the injection site 27. The sleeve 104 comprises, between its radial stop 113 and its bearing surface 105 an intermediate radial stop 109.

Still in the example depicted in FIGS. 30 to 34, the sleeve tube 106 is equipped at its distal end with an internal radial tooth 115. This internal tooth 115 may be in the form of a continuous or discontinuous annular bulge. The sleeve tube 106 comprises a region for holding 108, on which the user exerts force in order to carry out the injection operation as will be seen later on.

The injection assistance device 101 of FIG. 30 further comprises an intermediate ring 116 attached to the flange 6, the said intermediate ring 116 being continued in the distal direction by a tubular part 117 the distal end of which is provided with at least one external radial projection 118. This radial projection 118 comprises an inclined distal face 119.

The body 2 contains the product 25 that is to be injected and is closed off, at its opposite end to the needle 7, by a piston plunger 26 connected to the plunger rod 146.

The way in which the injection set 100 works will now be described with reference to FIGS. 31 to 34.

The injection set 100 is supplied at rest in the state depicted in FIG. 31. In this pre-use initial position, the sleeve 104 completely covers the needle 7. Thus, the injection set 100 is safe, any needlestick injury being avoided.

As can be seen in FIG. 31, the distal end of the first spring 110 bears against the proximal face of the said radial stop 113 and its proximal end bears against the distal face of the said intermediate ring 116. As far as the second spring 111 is concerned, its distal end bears against the proximal face of the radial rim 112 and its proximal end bears against the internal wall of the region for holding 108.

In FIG. 31, the first spring 110 can in the relaxed state or in a partially compressed state and the second spring 111 is in a partially compressed state. Thus, the sleeve 104 is retained, in terms of proximal translation with respect to the body 2, by the respective thrusts of the first and of the second spring 110, 111 and by, on the one hand, the distal face of the radial rim 112 bearing against the proximal face of the radial projection 118 and, on the other hand by the proximal face of the radial tooth 115 bearing against the distal face of the external radial step 114. In addition, the sleeve 104 is retained, in terms of distal translation with respect to the body 2, by the abutment of its intermediate radial stop 109 against the internal radial tooth 115 of the sleeve tube 106.

In order to perform the injection, the user grasps hold of the injection assistance device 101 via the sleeve tube 106, and places the bearing surface 105 of the sleeve 104 at right angles onto the surface of the injection site 27, as shown in FIG. 32.

Once the injection assistance device 101 is positioned in the desired location for the injection, the user exerts axial force in the distal direction on the region for holding 108 of the sleeve tube 106 in order to proceed with the phase of inserting the needle 7 into the injection site 27.

The sleeve tube 106 which is in direct contact with the plunger rod 146 will push it in the distal direction without any absorption of the force applied by any deformable means. As the force to overcome the stiction of the piston plunger 26 of the plunger rod 146 is greater than the force of compression of the first spring 110 combined with the force to overcome the friction of the penetration of the needle 7 in the injection site 27, the body 2 and plunger rod 146 assembly moves in the proximal direction under the action of the axial force, without the piston plunger 26 being moved within the body 2, as shown in FIG. 32. This movement causes the first spring 110 to become compressed. The needle 7 penetrates the injection site 27 until the inclined distal face 119 comes into abutment against the internal ramp 120.

Thus, the needle 7 has penetrated the injection site 27 to a perfectly defined insertion depth L as can be seen in FIG. 32. By virtue of the inclined distal face 119 coming into abutment against the internal ramp 120, it is then no longer possible to cause the needle 7 to penetrate any further into the injection site 27. The insertion depth L is thus perfectly controlled. The insertion depth L can be adjusted by using an intermediate ring 116 of a predetermined specific thickness.

Moreover, during this insertion step, the coupling means, that is to say the plunger rod 146, are mechanically rigid between the sleeve tube 6 and the body 2. In this insertion step, there is therefore no way to start moving distally the plunger rod 146 related to the barrel 2, therefore, no risk to start the injection before reaching the right insertion depth. The injection assistance device 101 of FIGS. 30 to 34 therefore ensures a two step use, with a first step for the insertion, and a second step for the injection.

Under the effect of an additional axial force on the region for holding 108 of the sleeve tube 106, the internal ramp 120 of the proximal end of the sleeve 140 presses against the inclined distal face 119 of the projection 118 and causes the third projection 118 to flex inwards, thus disengaging the projection 118 from the rim 112. This disengagement releases the second spring 111 which, in returning to its relaxed state, drives the plunger rod 146 in the distal direction, the said plunger rod 146 then automatically administering the injection by driving the piston plunger 26 which, in turn, expels the product 25 towards the needle 7, as shown in FIG. 33.

The device of FIGS. 30 to 34 therefore ensures a two step use, with a first step for the insertion, and a second step for the injection.

In an embodiment, not depicted, of the invention, the second spring 111 is kept in the compressed state by a button situated on the exterior wall of the sleeve tube 106, the said button being able to deflect and to release the second spring 111 under the effect of pressure by the user on the said button.

At the end of injection, as shown in FIG. 33, the injection depth of the needle 7 has not varied, the piston plunger 26 is at the end of its travel in the body 2 and the first spring 110 is still in the compressed state.

As can be seen on FIGS. 32 and 33, a gap 901 is present between the internal radial tooth 115 of the sleeve tube 106 and the intermediate radial stop of the sleeve 104.

During the injection step, the second spring 111 is a partially expanded state. Therefore, if during the injection step, the user, for instance by inadvertence, releases the distal pressure he exerts on the sleeve tube 106 when applying it on the injection site 27, causing thereby a limited proximal movement of said sleeve tube 106, then the spring 111, because it is in a partially expanded state and thanks to the presence of the gap 901, is allowed to dampen said proximal movement by expanding a little more and thereby causing the longitudinal skirt 148 of the plunger rod 146, and therefore the body 2, to be urged towards the site injection 27. The needle 7 is therefore maintained at a constant insertion length, namely its predetermined insertion length L.

To finish off the operation and make the injection assistance device 101 safe, the user then releases the force on the region for holding 108 of the sleeve tube 106 and withdraws the injection assistance device 101 from the injection site 27. As the pressure previously applied on the first spring 110 is suppressed, the first spring 110 automatically expands to return to its initial relaxed state as depicted in FIG. 34, thereby causing the deployment of the sleeve 104, which covers the needle 7. In this final protection position, the sleeve 104 is pressed against the sleeve tube 106 with the intermediate radial stop 109 of the sleeve 104 abutting against the internal radial tooth 115 of the sleeve tube 106.

During the deployment of the sleeve 104, a raised inclined plane (not depicted) situated on the wall of the longitudinal skirt 150 of the said sleeve tube 106 has collaborated with an inclined cam (not depicted) of the sleeve 104 to cause the sleeve 104 to turn with respect to the said sleeve tube 106, and the bringing of the said inclined plane into engagement in the said inclined cam prevents any translational movement of the said sleeve 104 with respect to the said sleeve tube 106.

Thus, in the final protection state depicted in FIG. 34, the injection set 100 is perfectly safe and can be discarded by the user without the risk of needlestick injury.

Another embodiment of the invention will now be described with reference to FIGS. 35 to 39.

References identical to FIGS. 30 to 34 have been maintained. The injection set 100 of FIG. 35 comprises a hollow body 2, a plunger rod 146, a sleeve 104 and a sleeve tube 106. The sleeve tube 106 defines a longitudinal skirt 150 of which the distal part, in the insertion position as depicted in FIG. 36, covers the proximal part of the sleeve 104. The injection set 100 also comprises an intermediate tubular component 136 and a spring 139.

The head of the plunger rod 146 is extended in the distal direction by a longitudinal skirt 148 the distal end of which is equipped with an external radial rim 112. The sleeve 104 comprises, formed in its wall, at least one longitudinal tab 127 extending in the proximal direction and able to deflect tangentially, the said tab 127 being equipped at its proximal end with an external radial peg 128, as shown in FIG. 39.

The sleeve tube 106 is in the form of two concentric cylindrical sheaths, an internal sheath 129 and an external sheath 130, joined together at their proximal ends by a transverse wall in the form of a circular band, this transverse wall together with the external sheath 130 constituting the region for holding 108 of the sleeve tube 106. The internal sheath 129 is attached to the flange 6 and housed inside the longitudinal skirt 148 of the plunger rod 146. At its distal end it comprises an external radial tooth 142, the utility of which will be explained later on.

The external sheath 130 houses the sleeve 104 and comprises, in its distal part, an inclined cam 132 formed on the wall of the said external sheath 130, the said cam 132 comprising a distal end 133 and a proximal end 134 and is able to collaborate with the peg 128 of the said tab 127, as shown in FIG. 39.

The external sheath 130 further comprises, situated on its internal wall and proximally with respect to the cam 132, a radial projection 135. The radial projection 135 comprises an inclined distal face 140, the utility of which will be explained later on.

The intermediate tubular component 136 is arranged between the longitudinal skirt 148 of the said plunger rod 146 and the external sheath 130, the said intermediate tubular component 136 comprising at its proximal end an internal radial step 137, the said tubular component 136 further comprising a notch 138 formed on its external wall.

The spring 139 is arranged between the longitudinal skirt 148 of the said plunger rod 146 and the external sheath 130. The distal end of the said spring 139 bearing against the proximal face of the internal radial step 137, the proximal end of the said spring 139 bearing against the distal face of the said transverse wall of the region for holding 108 in the form of a circular band.

Figure 35:
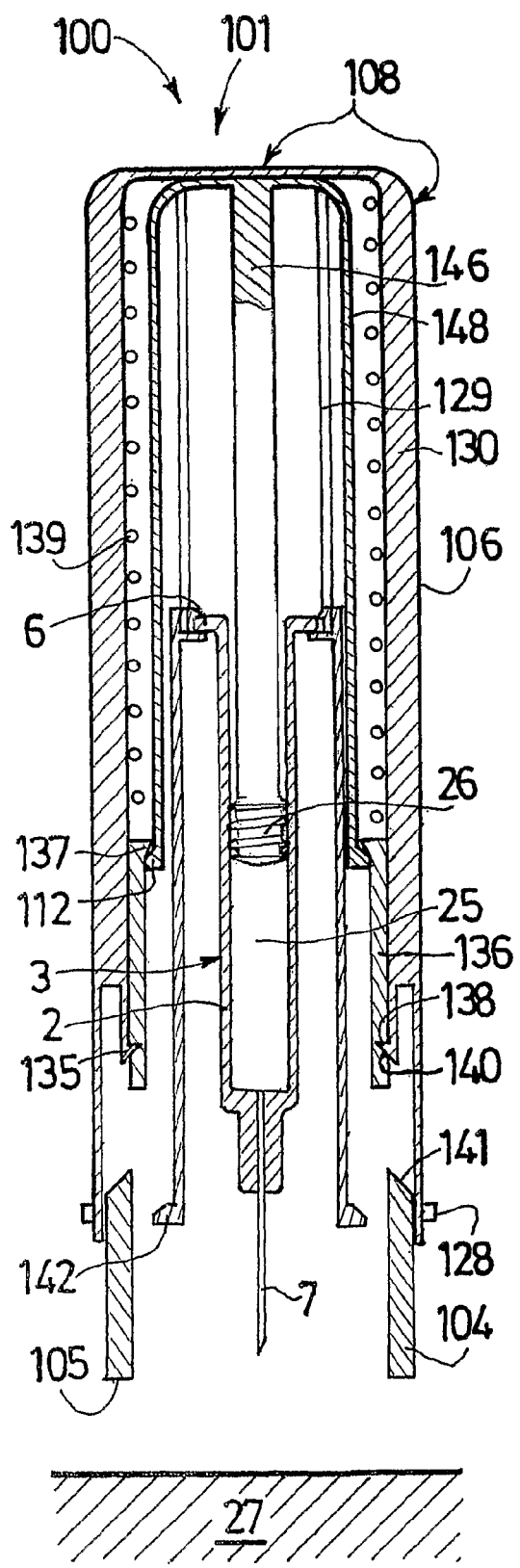
Figure 36:
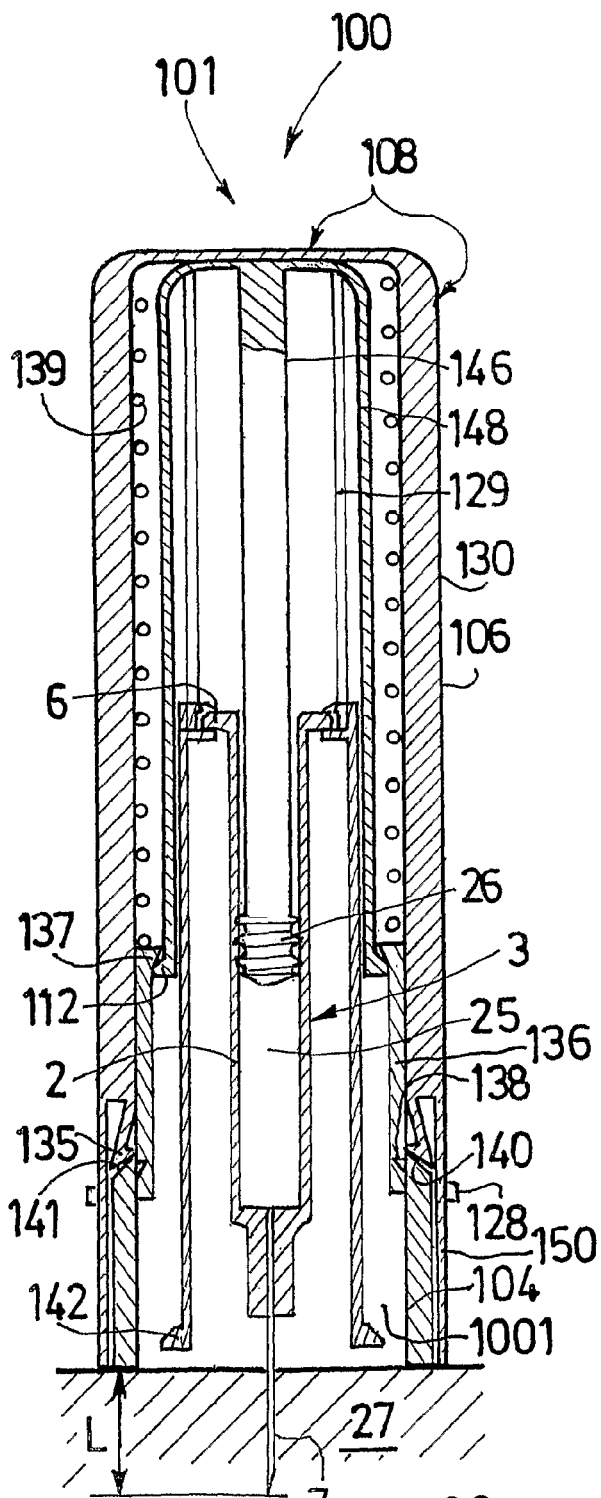

The injection assistance device 101 is supplied in the state depicted in FIG. 35. In this initial position, the spring 139 is in the compressed state and with the said radial projection 135 engaged in the said notch 138, the retaining means are formed of the thrust of the said spring 139 and the said radial step 137 coming to bear against the said radial rim 112 on the one hand, and the said peg 128 coming to bear against the distal end 133 of the said cam 132, on the other.

In order to proceed with the insertion and injection operations, the user grasps hold of the injection assistance device 101 via the sleeve tube 106 and places the bearing surface 105 of the sleeve 104 at right angles onto the surface of the injection site 27, as shown in FIG. 35.

Once the injection assistance device 101 is positioned at the desired location for the insertion, the user exerts an axial force in the distal direction on the region for holding 108 of the sleeve tube 106 in order to proceed with the phase of inserting the needle 7 into the injection site 27.

The sleeve tube 106 which is in direct contact with the plunger rod 146 will push it in the distal direction without any absorption of the force applied by any deformable means.

As the force needed to overcome the stiction of the piston plunger 26 of the plunger rod 146 is greater than the force of compression of the spring 139 combined with the force to overcome the friction of the penetration of the needle 7 into the injection site 27, the body 2, plunger rod 146 and sleeve tube 106 assembly moves in the proximal direction under the action of the axial force, without the piston plunger 26 moving within the body 2, as shown in FIG. 36. The needle 7 penetrates the injection site 27 until on the one hand the said inclined distal face 140 comes into abutment against the said external ramp 141 and, on the other hand, the said peg 128 comes into abutment against the proximal end 134 of the said cam 132, the said tab 127 being in the unflexed state.

Thus the needle 7 has penetrated the injection site 27 to a perfectly defined insertion depth L as can be seen from FIG. 36. It is then no longer possible to cause the needle 7 to penetrate any further into the injection site 27. The insertion depth L is thus perfectly controlled. In this example, the insertion depth L is directly linked with the dimension between the internal sheath 129 holding the flange 6 and the bearing surface 105 and/or of the intermediate tubular component 136, the cam 132. In an embodiment not depicted, the size of the sleeve tube 106 can be adjustable to allow adjustment of the insertion depth L.

Moreover, during this insertion step, the coupling means, that is to say the plunger rod 146, are mechanically rigid between the sleeve tube 6 and the body 2. In this insertion step, there is therefore no way to start moving distally the plunger rod 146 related to the barrel 2, therefore, no risk to start the injection before reaching the right insertion step. The injection assistance device 101 of FIGS. 35 to 39 therefore ensures a two step use, with a first step for the insertion, and a second step for the injection.

Under the effect of an additional axial force on the region for holding 108 of the sleeve tube 106, the external ramp 141 pushes the inclined distal face 140, the projection 135 unflexes radially outwards and disengages from the notch 138, releasing the spring 139 which deploys and carries with it the intermediate tubular component 136 and therefore the plunger rod 146 which then administers the injection by driving the piston plunger 26. The piston plunger 26 expels the product 25 towards the needle 7 as shown in FIG. 37. The injection is therefore administered automatically without additional manual intervention on the part of the user.

At the end of injection, as shown in FIG. 37, the piston plunger 26 is at the end of its travel in the closed end of the body 2 and the depth of insertion of the needle 7 has not varied.

In the insertion and injection positions the spring 139 is in a partially expanded state.

As can be seen from FIGS. 36 and 37, a gap 1001 is present between the intermediate tubular component 136 and the sleeve tube 106.

Therefore, if during the injection step, the user, for instance by inadvertence, releases the distal pressure he exerts on the sleeve tube 106 when applying it on the injection site 27, causing thereby a limited proximal movement of said sleeve tube 106, then the spring 139, because it is in a partially expanded state and thanks to the presence of the gap 1001, is allowed to dampen said proximal movement by expanding a little more and thereby causing the intermediate tubular component 136, and therefore the body 2, to be urged towards the site injection 27. The needle 7 is therefore maintained at a constant insertion length, namely its predetermined insertion length L.

To finish off the operation and make the injection set 100 safe, the user then releases the force on the region for holding 108 of the sleeve tube 106 and withdraws the injection set 100 from the injection site 27. The tab 127 is then no longer subjected to any pressure and returns to its unflexed state by elastic return, driving the sleeve 104 with it. Likewise, the spring 139 continues to deploy in order to reach its relaxed state, driving with it the said intermediate tubular component 136, the radial step 137 of the said intermediate tubular component 136 being able to unflex radially outwards under the action of the said spring 139 to disengage from the said radial rim 112 of the said plunger rod 146.

At the end of deployment of the spring 139, the proximal face of the radial step 137 of the intermediate tubular component 136 comes into abutment against the distal face of the external radial tooth 142 of the internal sheath 129 and the said intermediate component 136 is blocked in terms of translation with respect to the body 2.

Thus, in the final protection position depicted in FIG. 38, the injection assisted device 100 is completely safe and can be discarded by the user without the risk of needlestick injury.

In other forms of embodiment, not depicted, the helical springs may be replaced by leaf springs, pieces of elastomer, sealed gas chambers inside which the gas can be pressurized and expanded in succession, or any other equivalent means.

In reference to FIGS. 40 to 45, is represented an injection assistance device 201 according to the invention, intended to be used with an injection device 3 for administering via injection a product 25 into an injection site 27. The injection device 3 comprises a hollow body 2 for receiving the product 25 to be injected. The body 2 is provided at its tip 223 with an injection needle 7 intended to penetrate the injection site 27 as shown on FIG. 43.

Figures 44, 45:
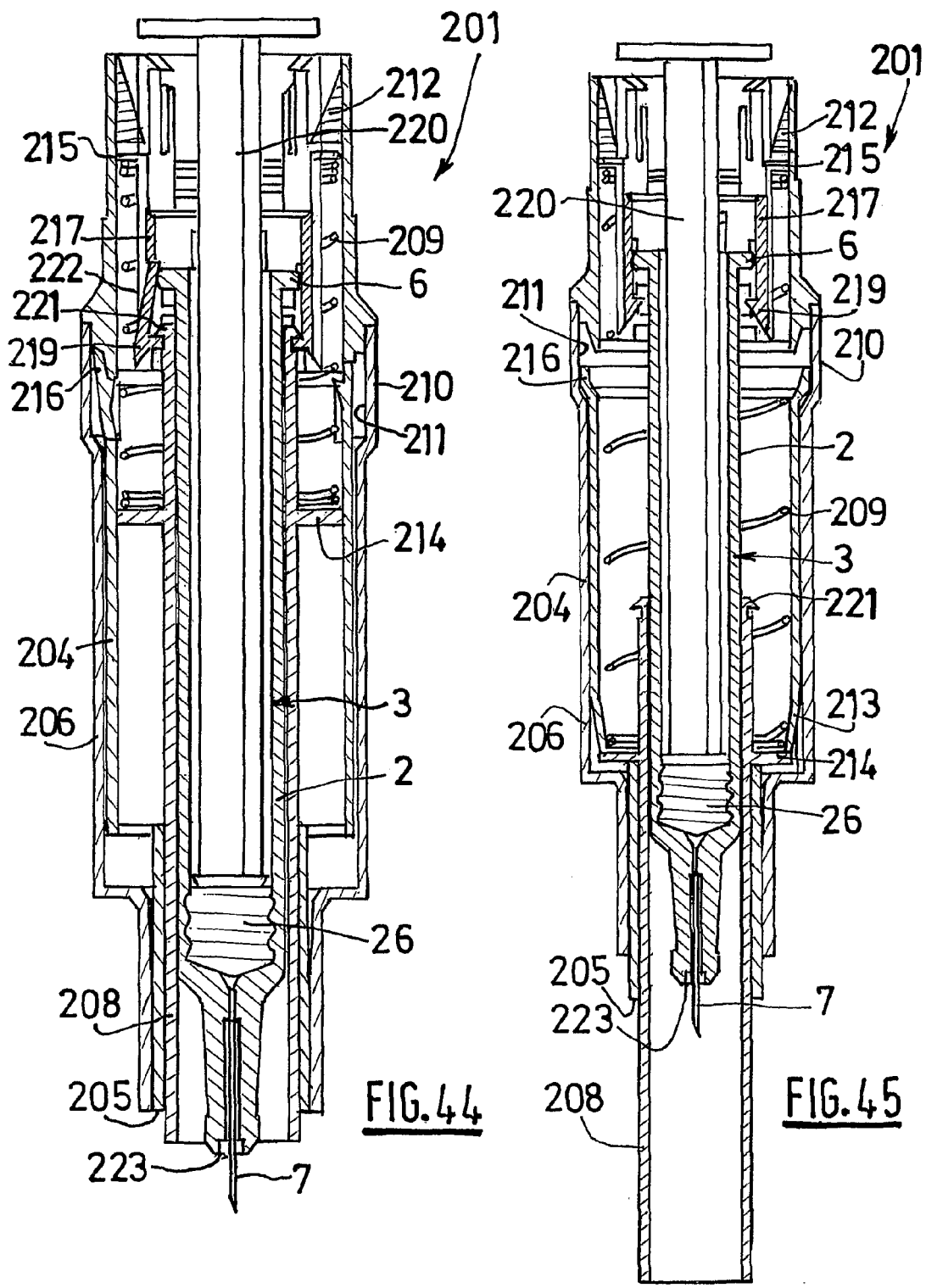

A piston plunger 26, as shown on FIG. 2, is housed in the body 2, said piston plunger 26 being able to be moved, by a plunger rod 220, in the example shown, in axial translation with respect to said body 2, in order to push said product 25 towards the distal end of said body 2 and therefore realize injection, as shown on FIGS. 43 and 44.

The injection assistance device 201 of FIGS. 40 to 45 comprises grasping means, under the form of an outer sleeve 206 in the example shown, which receives the body 2. In the example shown on FIGS. 40 to 45, the outer sleeve 206 is made of two parts, a proximal part 206a and a distal part 206b but alternatively said outer sleeve 206 could be one single integral part. Said body 2 is axially movable relative to said outer sleeve 206 from an initial position, in which the needle 7 is not exposed over the totality of its length, as shown on FIGS. 40-42, to an insertion position, distally spaced relative to said initial position, in which said needle 7 is exposed by a predetermined insertion length L, as shown on FIG. 43.

The outer sleeve 206 comprises, more or less in its middle region on the example shown, a portion of larger diameter 210 defining an inner recess 211, first angled abutting surfaces 241 and second angled abutting surfaces 242. Said outer sleeve 206 further comprises at least two flexible projections 212 defined on the inner wall of its proximal end.

The injection assistance device 201 of FIGS. 40 to 45 further comprises an actuating means, represented by an intermediate sleeve 204 in the example shown. Said intermediate sleeve 204 is received within said outer sleeve 206 and comprises a bearing surface 205 at its distal end, said bearing surface 205 being intended to bear on the injection site 27 as shown on FIG. 42. Said intermediate sleeve 204 is able to move relative to said outer sleeve 206 from a rest position, shown on FIG. 41 to a bearing position, as shown on FIG. 42.

The intermediate sleeve 204 is provided at its distal end with at least two flexible legs 213 and at its proximal end with at least two other flexible legs 216, which, in the initial position, bear on the inner wall of said outer sleeve 206 and, in the rest position, cooperate with said first angled abutting surfaces 241. The function of these legs will be explained hereinbelow.

The injection assistance device 201 of FIGS. 40 to 45 further comprises an inner sleeve 208 received within said intermediate sleeve 204. Said inner sleeve 208 is able to move axially relative to said body 2 from an injection position, in which the needle 7 is exposed, as shown on FIG. 43, to a protection position, in which said inner sleeve 208 covers said needle 7, as shown on FIG. 45.

In the insertion and injection positions shown on FIGS. 40 to 44, said inner sleeve 208 is coupled to said body 2 by means of a ring 217 in which a proximal flange 6 of said body 2 is clipped. The ring 217 comprises, at its distal end, at least two flexible teeth 219 which are engaged in at least two corresponding stops 221 formed at the proximal end of said inner sleeve 208, from the initial position to the insertion position, as shown on FIGS. 40 to 43. In the initial position as shown on FIG. 40, said flexible teeth 219 bear radially on an inner longitudinal wall 222 formed on the outer sleeve 206. In the rest position flexible teeth 219 are designed to cooperate with said second angled abutting surfaces 242 as explained hereinbelow.

The inner sleeve 208 comprises a radial rim 214 formed on its outer surface. As shown on FIG. 40, an helicoidal spring 209 is placed between the outer sleeve 206 and the inner sleeve 208: in the initial position, as shown on FIG. 40, said spring 209 is under tension, its proximal end bearing on a radial stop 215 formed on the inner wall of the proximal region of said outer sleeve 206 and its distal end bearing on said radial rim 214 of the inner sleeve 208.

The injection operation will now be explained in reference to FIGS. 40 to 45.

The user is provided with the assistance injection device 201 of the invention as shown on FIG. 40. In this position, the needle 7 is preferably covered by a protection cap 224 that the user removes before use. In this initial position, the body 2 is clipped in the ring 217 via its flange 6, said ring 217 being engaged with the inner sleeve 208 by engagement of its flexible teeth 219 in said stops 221 of the inner sleeve 208.

The body 2 is therefore maintained in its initial position by engagement of said radial rim 214 of the inner sleeve 208 with the flexible legs 216 of said intermediate sleeve 204, under the action of said helicoidal spring 209 which is under tension, said flexible legs 216 bearing radially on the inner wall of said outer sleeve 206.

Once the user has removed the protection cap 224, he can purge the injection device 3 by holding the injection assistance device 201 and pushing distally on the plunger rod 220. Once the purge is done, the user can carry on the distal movement of the plunger rod 220 to adjust the dose to be injected by expelling the product 25 in excess.

In order to perform the injection, the user grasps the injection assistance device 201 via the outer sleeve 206 and he applies said injection assistance device 201 on the injection site 27 via the bearing surface 205 of said intermediate sleeve 204, as shown on FIG. 41. In this position, the needle 7 is covered by said intermediate sleeve 204.

As shown on FIG. 42, the user further exerts a distal force on said outer sleeve 206, causing the intermediate sleeve 204 to move proximally relative to said outer sleeve 206, from a rest position, shown on FIG. 41, to a bearing position, shown on FIG. 42. This movement causes the distal translation of the recess 211 relative to said intermediate sleeve 204 and the flexible legs 216 are then deformed radially in the outward direction by said angled abutting surfaces 241, thereby freeing the radial rim 214, as shown on FIG. 42. The radial rim 214 is pushed distally by the spring 209, which tends to come back to its rest position, drawing altogether the inner sleeve 208, the ring 217 and the body 2, until the tip 223 of said body 2 enters in contact with the injection site 27, realizing the insertion of the needle 7 as shown on FIG. 43. In this insertion position, the needle 7 is inserted in the injection site 27 on a predetermined length L and the insertion depth is directly linked with the length of the needle 7.

In another embodiment not shown of the invention, the intermediate sleeve 204 is provided with internal abutments designed to stop the inner sleeve 208 in the insertion position before contact of the tip 223 with the injection site 27. In this case, the insertion depth L is not directly linked with the needle 7 length.

In another second embodiment not shown of the invention, during the injection, the extremity of the inner sleeve 208 is in contact with the injection site 27, allowing a gap between the injection site 27 and the tip 223. In this case, the insertion depth L depends on the difference between this gap and the needle 7 length.

According to FIG. 42, during the distal movement of the inner sleeve 208, the ring 217 and the body 2, the flexible projections 212 have allowed the passage in the distal direction of the ring 217. As shown on FIG. 43, the return of the ring 217 and by consequence of the body 2 in the proximal direction is now hindered by the distal surfaces of the flexible projections 212: this allows the user to complete a vein test, that is to say to check whether the needle 7 is in contact with a vein or not, by withdrawing the plunger rod 220 to determine whether some blood is drawn or not, without having to remove the needle 7 from the injection site 27.

The automatic insertion of the needle 7 according to the invention allows a reproductible length of insertion. The handling of the injection assistance device 201 is very simple for the user who does not have to check manually the insertion length.

As can be seen from FIG. 43, a gap 2001 is present between the ring 217 and the second angled abutting surfaces 242. Moreover, the spring 209 is in a partially expanded state.

Once the needle 7 is inserted, the combination of the gap 2001 between the ring 217 and the second angled abutting surfaces 242 plus the remaining possible extension of the spring 209 prevent the needle insertion length L modification, if the user inadvertently slightly removes the pressure on the outer sleeve 206. This enables to ensure the injection of the product 25 at the right depth.

On the contrary, if during the injection step, the user increases the distal pressure he exerts on the sleeve 206 when applying it on the injection site 27, causing thereby a limited distal movement of said outer sleeve 206, then the spring 209, because it is in a partially expanded state and thanks to the presence of the space 2002 between the radial stop 215 of the outer sleeve 206 and the radial rim 214 of the inner sleeve 208, coupled to the body 2, is allowed to dampen said distal movement by being compressed, thereby maintaining the needle 7 at a constant insertion length, namely its predetermined insertion length L.

The influence of any increase or release of the distal pressure exerted by the user on the outer sleeve 206 during injection is therefore neutralized by the presence of the spring 209 in a partially expanded state.

After the needle 7 is inserted, the user proceeds manually with the injection of the product 25 by pushing distally on the plunger rod 20.

According to the injection assistance device 201 shown on FIGS. 40 to 45, in order to adjust the dose of product 25 to be injected, the user may decide to stop the injection at any time without taking any risk of accidental needlestick injury when he removes the injection assistance device 201 from the injection site 27.

Indeed, when the user has decided that enough product 25 is injected, or at the end of injection, as shown on FIG. 44, the user removes the injection assistance device 201 from the site of injection 27. By this action, the tip 223 of said body 2 is no longer retained by the injection site 27. The body 2, which is coupled to the ring 217 and to the inner sleeve 208 is therefore drawn distally under the action of the spring 209, which tends to come back to its rest position. During this distal translation, the flexible teeth 219 move distally with respect to said inner longitudinal wall 222 of said outer sleeve 206, until they contact the second angled abutting surfaces 242. Then, the flexible teeth 219 are deformed radially in the outward direction by the second angled abutting surfaces 242, as shown on FIG. 44, and they free said stops 221 in which they were previously engaged.

The inner sleeve 208 is therefore released from said ring 217 and said body 2, and is drawn distally by said spring 209, which tends to come back to its rest position, until said inner sleeve 208 covers the needle 7, thereby realizing the protection of said needle 7, as shown on FIG. 45.

In the protection position, as shown on FIG. 45, the inner sleeve 208 is prevented from returning back in the proximal direction by means of flexible legs 213 of the intermediate sleeve 204 which are engaged with said radial rim 214, the intermediate sleeve 204 abutting against the proximal part of the outer sleeve 206.

The injection assistance device 201 is therefore perfectly safe for the user and risks of accidental needlestick injuries are prevented.

In reference to FIGS. 46 to 51, is represented another variant of an injection assistance device 201 according to the invention. The references designating the same elements as in FIGS. 40 to 45 have been maintained. The injection assistance device 201 of FIGS. 46-51 is intended to be used with an injection device 3 for injecting a product 25 into an injection site 27. The injection device 3 comprises a hollow body 2 for receiving the product 25 to be injected. The body 2 is provided at its tip 223 with an injection needle 7 intended to penetrate the injection site 27 as shown on FIG. 47.

A piston plunger 26 is housed in the body 2, said piston plunger 26 being able to be moved, by a plunger rod 220, in the example shown, in axial translation with respect to said body 2, in order to push said product 25 towards the tip 23 of said body 2 and therefore realize injection, as shown on FIGS. 47 and 48.

The injection assistance device 201 of FIGS. 46 to 512 comprises an outer sleeve 228 which partially receives the body 2. Said body 2 is axially movable relative to said outer sleeve 228 from an initial position, in which the needle 7 is not exposed, as shown on FIG. 7, to an insertion position, distally spaced relative to said initial position, in which said needle 7 is exposed by a predetermined insertion length L, as shown on FIGS. 47 and 48.

The outer sleeve 228 is formed of a single piece having a proximal region 228a and a distal region 228b. The distal end of said proximal region 228a is provided with at least two flexible legs 229 and the proximal end of said proximal region 228a is provided with at least two flexible teeth 230 shown on FIG. 50.

The injection assistance device 201 of FIGS. 46 to 51 further comprises an inner sleeve 231, having a proximal region 231a and a distal region 231b of lesser diameter than said proximal region 231a, said proximal region 231a being connected to said distal region 231b by a radial wall 231c. Said proximal region 231a is received partially within said outer sleeve 228 and comprises, at its proximal end, two proximal projections 232. Said inner sleeve 231 comprises a bearing surface 205 at the distal end of its distal region 231b, said bearing surface 205 being intended to bear on the injection site 27 as shown on FIGS. 47 and 48.

Said inner sleeve 231 is able to move relative to said outer sleeve 228 from a rest position, shown on FIG. 46 to a bearing position, as shown on FIG. 47.

The inner sleeve 231 is able to move axially relative to said body 2 from an injection position, in which the needle 7 is exposed, as shown on FIGS. 47 to 50, to a protection position, in which said inner sleeve 231 covers said needle 7, as shown on FIG. 51.

The injection assistance device 201 of FIGS. 46 to 51 further comprises a ring 233 receiving partially the proximal region of said body 2, said ring 233 being coupled to said body 2 by means of two prongs (not shown) that clip a proximal flange 6 of said body 2.

Said ring 233 is provided with a flexible skirt 234 extending in the distal direction and able to be deformed radially, said flexible skirt 234 comprising at its distal end a outer radial rim 235.

Said ring 233 is prolongated toward the distal direction and surrounds the body 2.

The injection assistance device 201 of FIGS. 45 to 51 further comprises an annular rim 236 which is coupled to said ring 233 at least from the initial position to the insertion position by contact on the radial rim 235.

The injection assistance device 201 of FIGS. 46 to 51 also comprises a plunger rod 220, the distal end of which is screwed to said piston plunger 26. The plunger rod 220 is intended to be manually pushed in the distal direction to cause the axial translation of said piston plunger 26 in said body 2 in the distal direction in order to realize injection.

Said plunger rod 220 comprises at its proximal end a head 237 provided with a distal skirt 238 extending longitudinally in the distal direction, the proximal end of said head 237 being provided with an outer bevel 239.

The injection assistance device 201 of FIGS. 46 to 51 also comprises a gasket 240 which is coupled to said plunger rod 220 from the end of injection position to the protection position, as shown on FIGS. 50 and 51.

An helicoidal spring 209 is placed between the outer sleeve 228 and the ring 233: in the initial position, as shown on FIG. 46, said spring 209 is under tension, its proximal end bearing on the distal surface of said gasket 240 and its distal end bearing on the proximal surface of said annular rim 236.

The injection operation will now be explained in reference to FIGS. 46 to 51.

The injection assistance device 201 of the invention is provided to the user in its initial position shown on FIG. 46. In this initial position, the body 2 is clipped in the ring 233 via its flange 6. Said body 2 is therefore maintained in its initial position by the fact that said ring 233 is engaged with the outer sleeve 228 by cooperation of said flexible skirt 234, said annular rim 236, said flexible leg 229 and said helicoidal spring 209.

As appears from FIG. 46, in the initial position, the needle 7 is covered by said inner sleeve 231, in particular by said distal region 231b of said inner sleeve 231.

The user grasps the injection assistance device 201 by the outer sleeve 228, for example by its distal region 228b, and he applies said injection assistance device 201 on the injection site 27 via the bearing surface 205 of said inner sleeve 231.

As shown on FIG. 47, the user further exerts a distal force on said outer sleeve 228, causing the inner sleeve 231 to move proximally relative to said outer sleeve 228, from a rest position, shown on FIG. 46, to a bearing position, shown on FIG. 47. This movement causes the distal translation of the flexible legs 229 which come in contact with said proximal projections 232 of said inner sleeve 231. The flexible legs 229 are therefore caused to deform radially in the outward direction, as shown on FIG. 47, thereby freeing the annular rim 236. The annular rim 236 is pushed distally by the spring 209, which tends to come back to its rest position, drawing with him the ring 233 and the body 2, until the tip 223 of said body 2 enters in contact with the injection site 27, realizing the insertion of the needle 7 as shown on FIG. 47. In this insertion position, the needle 7 is inserted in the patient on a predetermined insertion length L.

In another embodiment of the invention not shown, the inner sleeve 231 is provided with internal abutments designed to stop the ring 233 in the insertion position before contact of the tip 223 with the injection site 27. In this case, the insertion depth L is not directly linked with the length of the needle 7.

In another second embodiment not shown of the invention, during the injection, the extremity of the inner sleeve 208 is in contact with the injection site 27, allowing a gap between the injection site 27 and the tip 223. In this case, the insertion depth L depends on the difference between this gap and the needle 7 length.

As seen before, the automatic insertion of the needle 7 according to the invention allows a reproductible length of insertion. The handling of the injection assistance device 201 is very simple for the user who does not have to check manually the insertion length.

Once the needle 7 is inserted, the combination of the gap 2001 between the outer sleeve 228 and the inner sleeve 231 plus the remaining possible extension of the spring 209 prevent the needle insertion length L modification, if the user inadvertently slightly removes the pressure on the outer sleeve 228. This enables to ensure the injection of the product 25 at the right depth.

On the contrary, if during the injection step, the user increases the distal pressure he exerts on the outer sleeve 228 when applying it on the injection site 27, causing thereby a limited distal movement of said outer sleeve 228, then the spring 209, because it is in a partially expanded state and thanks to the presence of the space 2002 between the flexible legs 229 and the inner sleeve 231, is allowed to dampen said distal movement by being compressed, thereby maintaining the needle 7 at a constant insertion length, namely its predetermined insertion length L.

The influence of any increase or release of the distal pressure exerted by the user on the outer sleeve 228 during injection is therefore neutralized by the presence of the spring 209 in a partially expanded state.

Once the needle 7 is inserted, the user proceeds manually with the injection of the product 25 by pushing distally on the plunger rod 220. As appears from FIG. 47, the flexible skirt 234 of the ring 233 is engaged with said annular rim 236 during the totality of the injection operation: in this way, even if the user decides to remove the injection assistance device 201 from the injection site 27 before the end of injection, that is to say before said piston plunger 26 has finished its course at the distal end of said body 2, then, the inner sleeve 231 remains in its injection position and does not cover the needle 7, thus allowing the user to carry on the injection if desired.

At the end of injection, as shown on FIG. 48, when the piston plunger 26 comes in contact with the distal end of said body 2, the distal force exerted by the user on the plunger rod 220 causes the distal skirt 238 to come into contact with said flexible skirt 234 of said ring 233 and to deform radially in the inward direction said flexible skirt 234, thereby freeing said annular rim 236.

The annular rim 236 is pushed distally by the spring 209, which tends to come back to its rest position, until it is stopped by the proximal surface of the radial wall 231c connecting said proximal region 231a to said distal region 231b of said inner sleeve 231.

The user then maintains the outer sleeve 228 while continuing to apply a distal force on said plunger rod 220 as shown on FIGS. 49 and 50. By this action, the bevels 239 of said plunger rod 220 come into contact with the flexible teeth 230 formed at the proximal end of said outer sleeve 228 and cause the radial deformation of said teeth in the outward direction, thereby freeing said gasket 240.

The user then removes the injection assistance device 201 from the injection site 27, as shown on FIG. 51. Said spring 209 then tends to come back to its rest position and pushes proximally on said gasket 240. Said gasket 240 pushes proximally on the head 237 of said plunger rod 220 which therefore draws said body 2 in the proximal direction, until said needle 7 is completely withdrawn within said inner sleeve 231 as shown on FIG. 51.

The injection sets and the injection assistance devices according to the invention are particularly simple to use and are perfectly safe. The entire injection operation can easily be performed by a single uni-directional axial movement, with just one hand. Moreover, the device of the invention ensures a two step use, with a first step for the insertion, and a second step for the injection. There is therefore no way to start the injection before reaching the right insertion step. The devices ensure a predetermined stable insertion depth during the injection step even despites slight movement of the user hand.

In addition, the injection sets and the injection assistance devices according to the invention enable the user to adjust the dose to be injected before proceeding with any injection step and/or to perform a vein test to prevent injection in the vein.

The invention claimed is:

1. Injection assistance device for an injection device for injecting a product into an injection site, this injection assistance device comprising at least one hollow body intended to receive a product that is to be injected, at least one hollow injection needle intended to penetrate the injection site, and at least one piston plunger housed in said body, and said piston plunger being able to be moved in axial translation one with respect to the other, said injection assistance device comprises at least:

sleeve intended to be manually handled by the user in order to apply said injection device on said injection site during an insertion and an injection steps, said sleeve being intended to receive at least in part, said body and being arranged in such a way as to allow said body axial mobility between at least a first position known as the initial position in which said needle is not exposed over its insertion length, and a second position known as the insertion position in which said needle is exposed by a predetermined insertion length L, at least a first spring coupled to said body and to said sleeve, said first spring being in a partially expanded state so as to dampen limited movement of said sleeve, in at least one of the two directions, respectively distal or proximal, during said injection step, and to maintain said body in its insertion position and said needle at a constant insertion length, namely said predetermined insertion length L, during the injection step, when the user increases, respectively releases, a distal pressure on the sleeve, an intermediate ring arranged in such a way as to cover said needle in a post-injection final protection position, which said intermediate ring is fixed to said body in the initial position so as to not be able to move in translation with respect to said body, said intermediate ring able to move in translation with respect to said body between an injection position in which the needle is exposed and a final protection position in which the needle is covered by said intermediate ring, said injection device being arranged in such a way that, in the insertion position, said sleeve is separated from said body, by a gap that allows said sleeve to move proximally with respect to said body, when distal pressure exerted on said sleeve is released with said first spring urging said needle distally relative to said sleeve towards said predetermined insertion length L;

wherein said sleeve includes an inwardly extending step arranged in such a way as to delimit said insertion position of said body.

2. Injection assistance device according to claim 1, wherein said first spring is arranged so as to dampen any limited distal or proximal movement of said sleeve during said injection step, and to maintain said body in its insertion position and said needle at a constant insertion length, namely said predetermined insertion length L, during the injection step, regardless of any increase or release of distal pressure exerted by the user on the sleeve.

3. Injection assistance device according to claim 1, wherein, in the insertion position, said sleeve is separated from said body, or from an element coupled to said body at least in said insertion position, by a space that allows the said sleeve to move distally with respect to said body or to said element, when distal pressure exerted on said sleeve is increased with said first spring compressing to allow proximal movement of said needle relative to said sleeve towards said predetermined insertion length L.

4. Injection assistance device according to claim 1, further comprising a coupling arranged in such a way as to move the said piston plunger from the said insertion position to an end-of-injection position and to inject said product.

5. Injection set for injecting a product into an injection site, the said injection set comprising at least:
   an injection device comprising at least:
      a hollow body intended to receive a product that is to be injected, the said body being equipped with a hollow injection needle intended, during a first phase known as the insertion phase, to penetrate an injection site and, during a second phase known as the injection phase, to channel the said product from the said body towards the said injection site,
      at least one piston plunger housed in a more or less sealed manner in the said body and intended to be moved in the distal direction in the said injection phase during which it drives the said product through the said needle,
   characterized in that it comprises at least an injection assistance device for assisting with the injection device according at least to claim 1.

6. Injection set according to claim 5, wherein the injection set is in the form of a kit that can be assembled prior to use.

7. Injection assistance device according to claim 1, wherein said sleeve is closed at a proximal end.

* * * * *

UNITED STATES PATENT AND TRADEMARK OFFICE
CERTIFICATE OF CORRECTION

PATENT NO. : 8,696,625 B2  Page 1 of 1
APPLICATION NO. : 11/912249
DATED : April 15, 2014
INVENTOR(S) : Carrel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1399 days.

Signed and Sealed this
Twenty-ninth Day of September, 2015

Michelle K. Lee
*Director of the United States Patent and Trademark Office*